US007485416B2

(12) United States Patent
Ott et al.

(10) Patent No.: US 7,485,416 B2
(45) Date of Patent: Feb. 3, 2009

(54) SCREENING METHODS FOR THE IDENTIFICATION OF AGENTS THAT INHIBIT SIRT1 TAT DEACETYLASE ACTIVITY

(75) Inventors: Melanie Ott, San Francisco, CA (US); Eric M. Verdin, San Francisco, CA (US); Manfred Jung, Freiburg (DE)

(73) Assignee: The Regents of the University of California, Oakland, CA (US)

( * ) Notice: Subject to any disclaimer, the term of this patent is extended or adjusted under 35 U.S.C. 154(b) by 322 days.

(21) Appl. No.: 11/022,192

(22) Filed: Dec. 22, 2004

(65) Prior Publication Data

US 2005/0287597 A1 Dec. 29, 2005

Related U.S. Application Data

(60) Provisional application No. 60/532,405, filed on Dec. 23, 2003.

(51) Int. Cl.
*C12Q 1/70* (2006.01)
*A61K 39/21* (2006.01)
(52) U.S. Cl. ........................ 435/5; 424/208.1
(58) Field of Classification Search .................... 435/5; 424/208.1
See application file for complete search history.

(56) References Cited

U.S. PATENT DOCUMENTS

2003/0082668 A1 5/2003 Tamai et al.

FOREIGN PATENT DOCUMENTS

WO WO 03/046207 6/2003

OTHER PUBLICATIONS

Voelter-Mahlknecht, S., and U. Mahlknecht, 2006, Cloning, chromosomal characterization and mapping of the NAD-dependent histone deacetylases gene sirtuin 1, Intl. J. Mol. Med. 17:59-67.*
Pagans, S., et al. SIRT1 regulates HIV transcription via tat deacetylation. PLoS Biology. 2005, vol. 3, No. 2, pp. 210-220.
Posakony, J., et al. Inhibitors of Sir2: Evaluation of splitomicin analogues. Journal of Medicinal Chemistry. 2004, vol. 47, pp. 2635-2644.
Rettinger, J., et al. The suramin analogue NF279 is a novel and potent antagonist selective for the P2X1 receptor. Neuropharmacology. 2000, vol. 39, pp. 2044-2053.
Sauve, A., et al. The biochemistry of sirtuins. Annual Review of Biochemistry. 2006, vol. 75, pp. 435-465.
Soto, F., et al. Anatagonistic properties of the suramin analogue NF023 at heterologously expressed P2X receptors. Neuropharmacology. 1999, vol. 38, pp. 141-149.
"SIRT1 Deacetylates the HIV Tat Protein and is Required for Tat-Mediated Transactivation of the HIV Promoter" Title, Workshop 1, Molecular Mechanisms of HIV Pathogenesis, Keystone Symposia, Whistler, British Columbia, [online] Apr. 12-18, 2004. Retrieved from the internet: URL: http://www.keystonesymposia.org/Meetings/ViewPastMeetings.cfm?MeetingID=694> [retrieved on Dec. 3, 2007].
Bedalov et al. (2001) Proc. Natl. Acad. Sci. USA 98:15113-15118.
Rusnati et al. (1998) J. Biol. Chem. 273:16027-16037.
Bitterman et al. (2002) J. Biol. Chem. 277:45099-45107.
Hirao et al. (2003) J. Biol. Chem. 278:52773-52782.
Kwon et al. Human immunodeficiency virus type 1 Tat protein inhibits the SIRT1 deacetylase and induces T cell hyperactivation. Cell Host Microbe. Mar. 13, 2008;3(3):158-67.

* cited by examiner

*Primary Examiner*—Jeffrey S. Parkin
(74) *Attorney, Agent, or Firm*—Paula A. Borden; Bozicevic, Field & Francis LLP

(57) ABSTRACT

The present invention provides treatment methods involving modulating a sirtuin activity and/or a sirtuin mRNA and/or a sirtuin polypeptide level. In some embodiments, the present invention provides treatment methods involving modulating SIRT1 activity and/or SIRT mRNA and/or polypeptide level. The present invention provides methods of inhibiting SIRT1 Tat deacetylase activity. Methods of inhibiting SIRT1 Tat deacetylase activity are useful for treating immunodeficiency virus infections, particularly human immunodeficiency virus (HIV) infection. Thus, the present invention provides methods of treating an immunodeficiency virus infection, generally involving inhibiting SIRT1 Tat deacetylase activity. The present invention further provides methods of identifying agents that modulate sirtuin activity (e.g., SIRT1 activity), particularly ability of sirtuins to interact with (e.g., bind and/or deacetylate) a substrate, e.g., a viral substrate such as a Tat polypeptide. The present invention further provides active agents that modulate sirtuin activity or expression; and compositions, including pharmaceutical compositions, comprising the active agents.

16 Claims, 11 Drawing Sheets

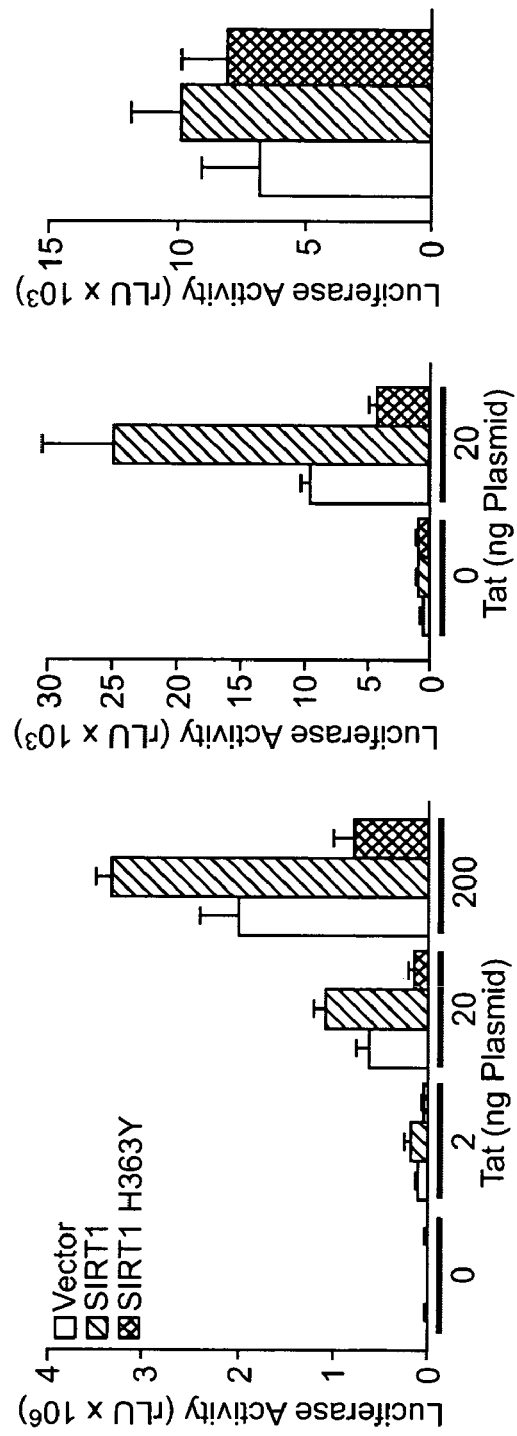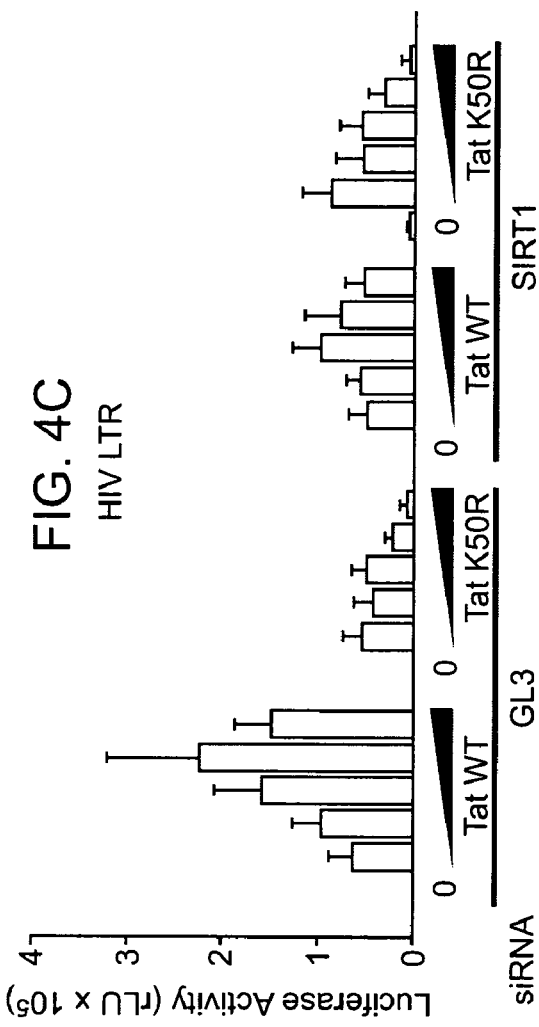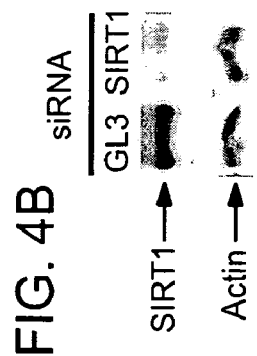
FIG. 4A
FIG. 4B
FIG. 4C

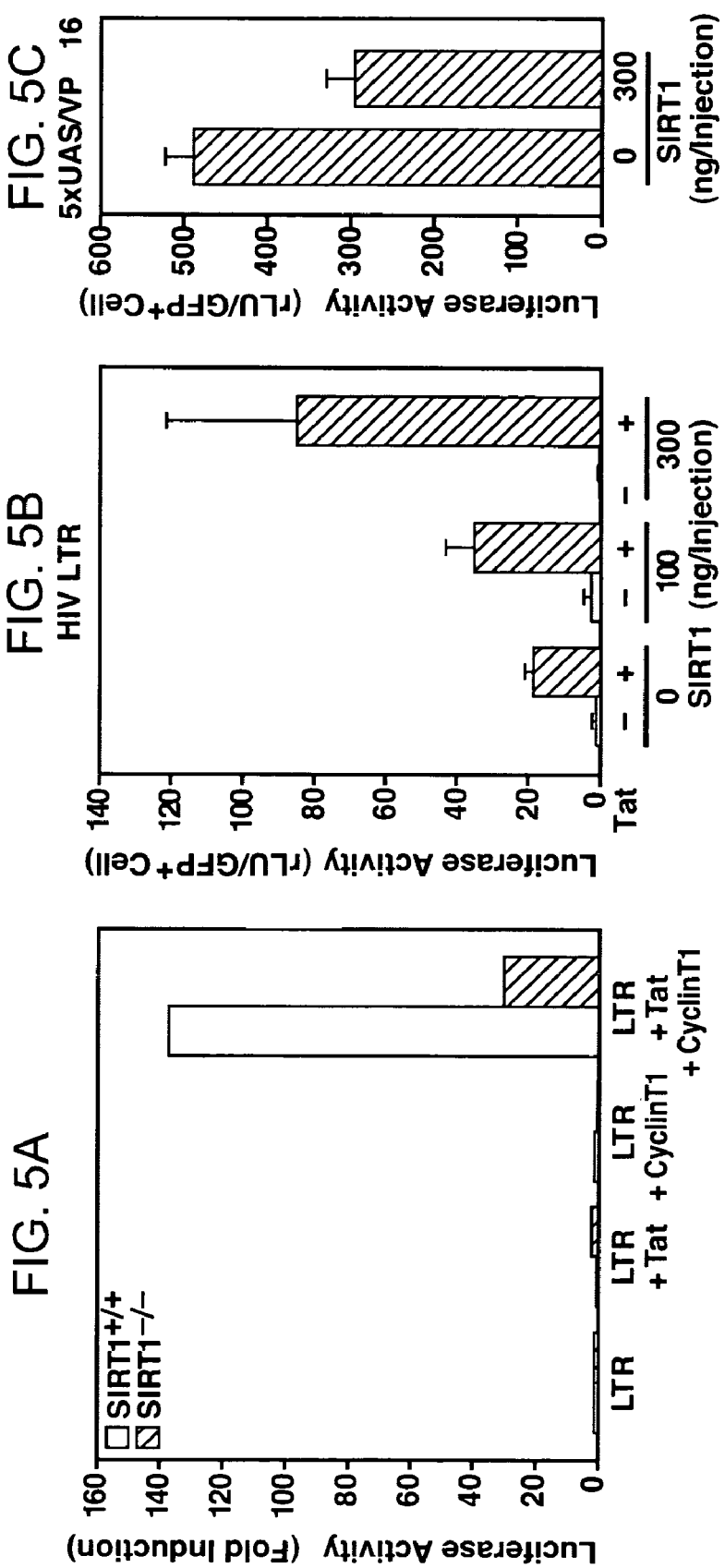

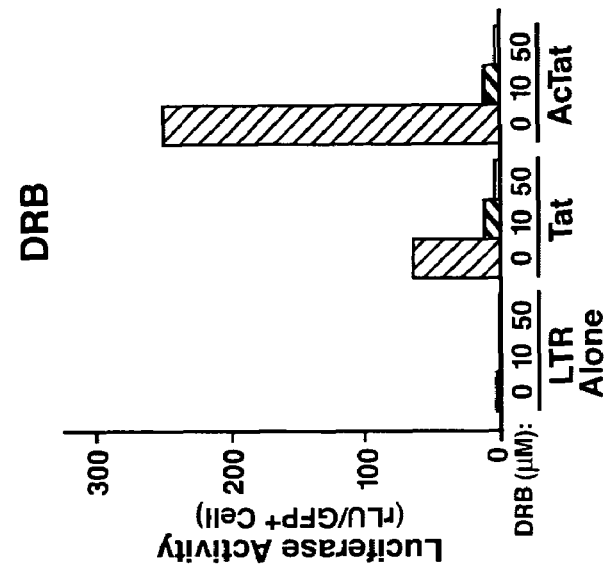
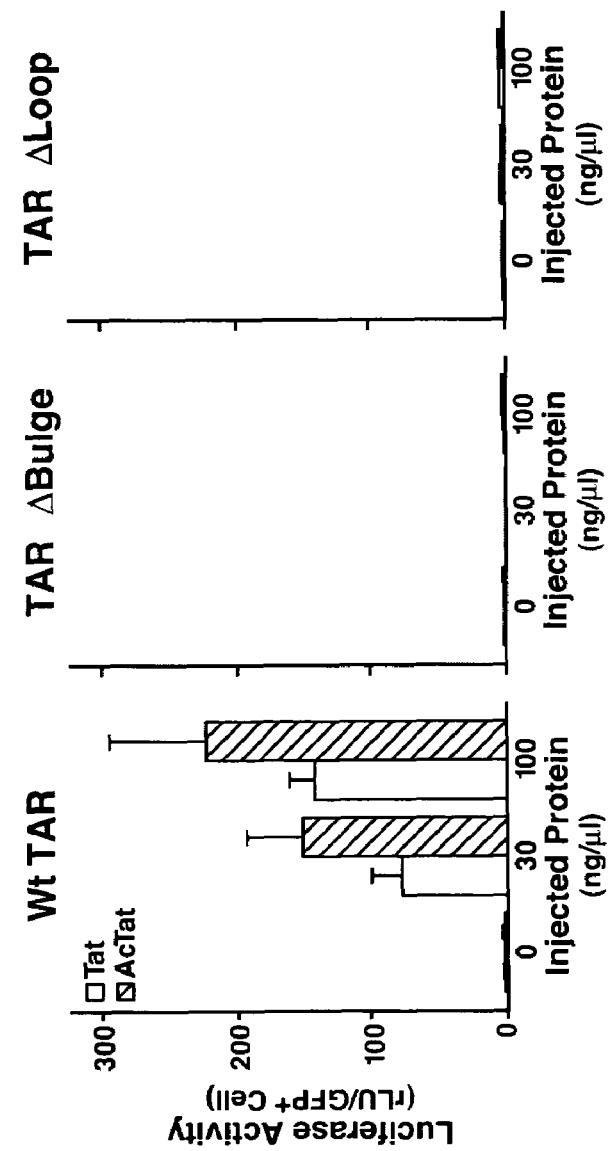
FIG. 6A
FIG. 6B

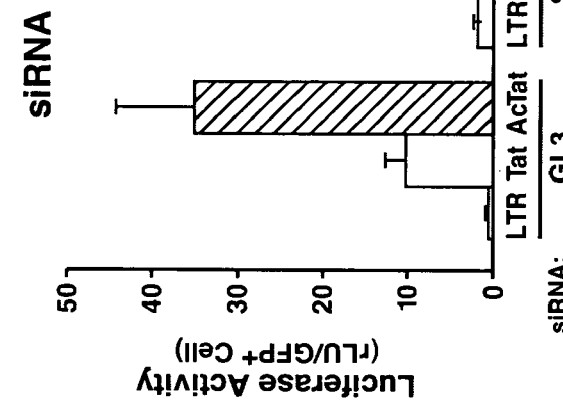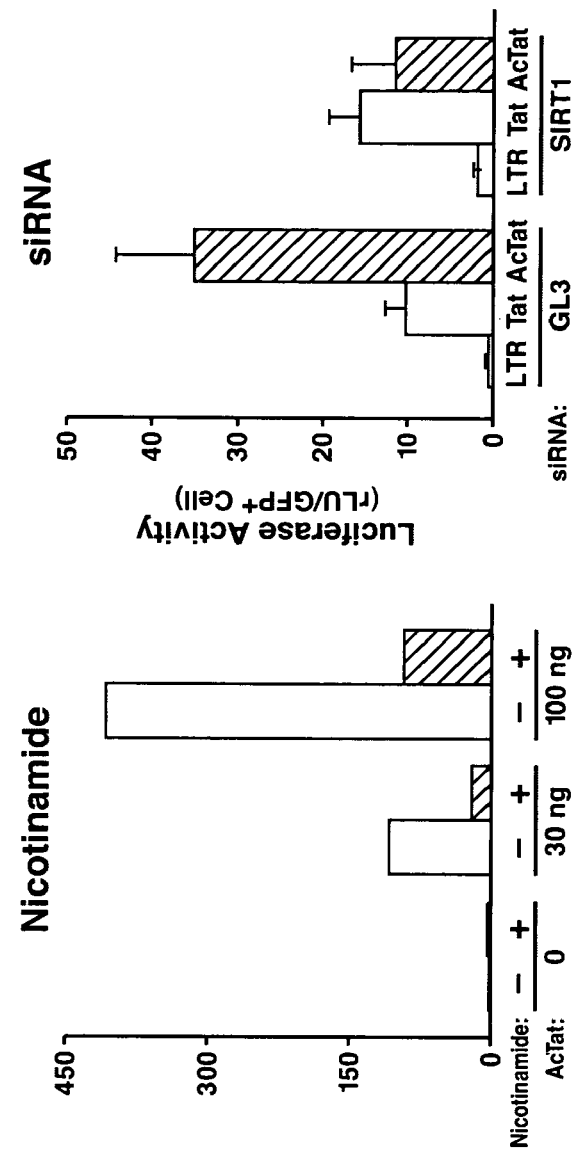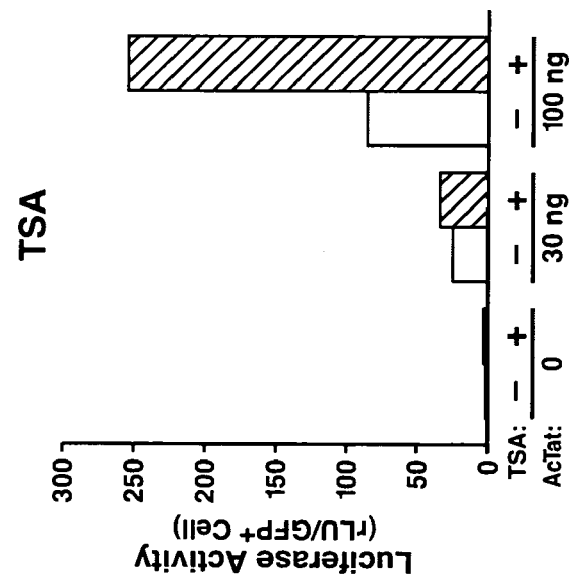
FIG. 6C
FIG. 6D

SCREENING METHODS FOR THE IDENTIFICATION OF AGENTS THAT INHIBIT SIRT1 TAT DEACETYLASE ACTIVITY

CROSS-REFERENCE

This application claims the benefit of U.S. Provisional Patent Application No. 60/532,405, filed Dec. 23, 2003, which application is incorporated herein by reference in its entirety.

STATEMENT REGARDING FEDERALLY SPONSORED RESEARCH

The U.S. government may have certain rights in this invention, pursuant to grant no. PO1GM066531 awarded by the National Institutes of Health.

FIELD OF THE INVENTION

The present invention is in the field of modulating sirtuin activity and in the field of treatment of immunodeficiency virus infections.

BACKGROUND OF THE INVENTION

Human immunodeficiency virus (HIV) is the etiologic agent of acquired immunodeficiency syndrome (AIDS). HIV infection leads to depletion of CD4+ T lymphocytes. AIDS is characterized by various pathological conditions, including immune incompetence, opportunistic infections, neurological dysfunctions, and neoplastic growth.

Transcriptional activity of the integrated HIV-1 provirus is regulated by the concerted action of cellular transcription factors and the viral transactivator Tat. In the absence of Tat, HIV transcription is highly inefficient because the assembled RNA polymerase II complex cannot elongate efficiently on the viral DNA template. Tat is a unique viral transactivator that binds to an RNA stem-loop structure called TAR, which forms at the 5' extremity of all viral transcripts. Tat binds to TAR via its C-terminal arginine-rich motif (amino acids 49-57) that is essential for RNA binding and nuclear localization. The N-terminal transactivation domain of Tat (amino acids 1-48) interacts directly with CyclinT1, a component of the positive-acting transcription elongation factor (P-TEFb) complex. CyclinT1 recruits the cyclin-dependent kinase 9 (CDK-9), the catalytic subunit of the separately identified "Tat-associated kinase" (TAK). TAK/CDK-9 hyperphosphorylates the C-terminal domain (CTD) of the large subunit of the RNA polymerase II (RNApolII), leading to increased elongation efficiency of the polymerase complex.

Several drugs have been approved for treatment of AIDS, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). However, none of the available drugs used to combat HIV is completely effective, and treatment frequently gives rise to drug-resistant virus.

Despite the availability of a number of drugs to combat HIV infections, there is a need in the art for additional drugs that treat HIV infections. The present invention addresses this need.

Literature

Bedalov et al. (2001) Proc. Natl. Acad. Sci. USA 98:15113-15118; Rusnati et al. (1998) J. Biol. Chem. 273:16027-16037; U.S. Patent Publication No. 20030082668; Bitterman et al. (2002) J. Biol. Chem. 277:45099-45107; Hirao et al. (2003) J. Biol. Chem. 278:52773-52782; and WO 03/046207.

SUMMARY OF THE INVENTION

The present invention provides treatment methods involving modulating a sirtuin activity and/or a sirtuin mRNA and/or a sirtuin polypeptide level. In some embodiments, the present invention provides treatment methods involving modulating SIRT1 activity and/or SIRT mRNA and/or polypeptide level. The present invention provides methods of inhibiting SIRT1 Tat deacetylase activity. Methods of inhibiting SIRT1 Tat deacetylase activity are useful for treating immunodeficiency virus infections, particularly human immunodeficiency virus (HIV) infection. Thus, the present invention provides methods of treating an immunodeficiency virus infection, generally involving inhibiting SIRT1 Tat deacetylase activity. The present invention further provides methods of identifying agents that modulate sirtuin activity (e.g., SIRT1 activity), particularly ability of sirtuins to interact with (e.g., bind and/or deacetylate) a substrate, e.g., a viral substrate such as a Tat polypeptide. The present invention further provides active agents that modulate sirtuin activity or expression; and compositions, including pharmaceutical compositions, comprising the active agents.

BRIEF DESCRIPTION OF THE DRAWINGS

FIGS. 3A-3E depict the results of experiments showing physical interaction between Tat and SIRT1 proteins.

FIGS. 4A-4F depict the results of experiments showing the role of SIRT1 as a positive cofactor for Tat transactivation.

FIGS. 5A-5C depict impaired Tat transcriptional activity in murine SIRT1$^{-/-}$ cells.

FIGS. 6A-6D depict results of experiments showing the role of SIRT1-mediated Tat deacetylation on transcriptional activity of AcTat.

DEFINITIONS

Figure 1:
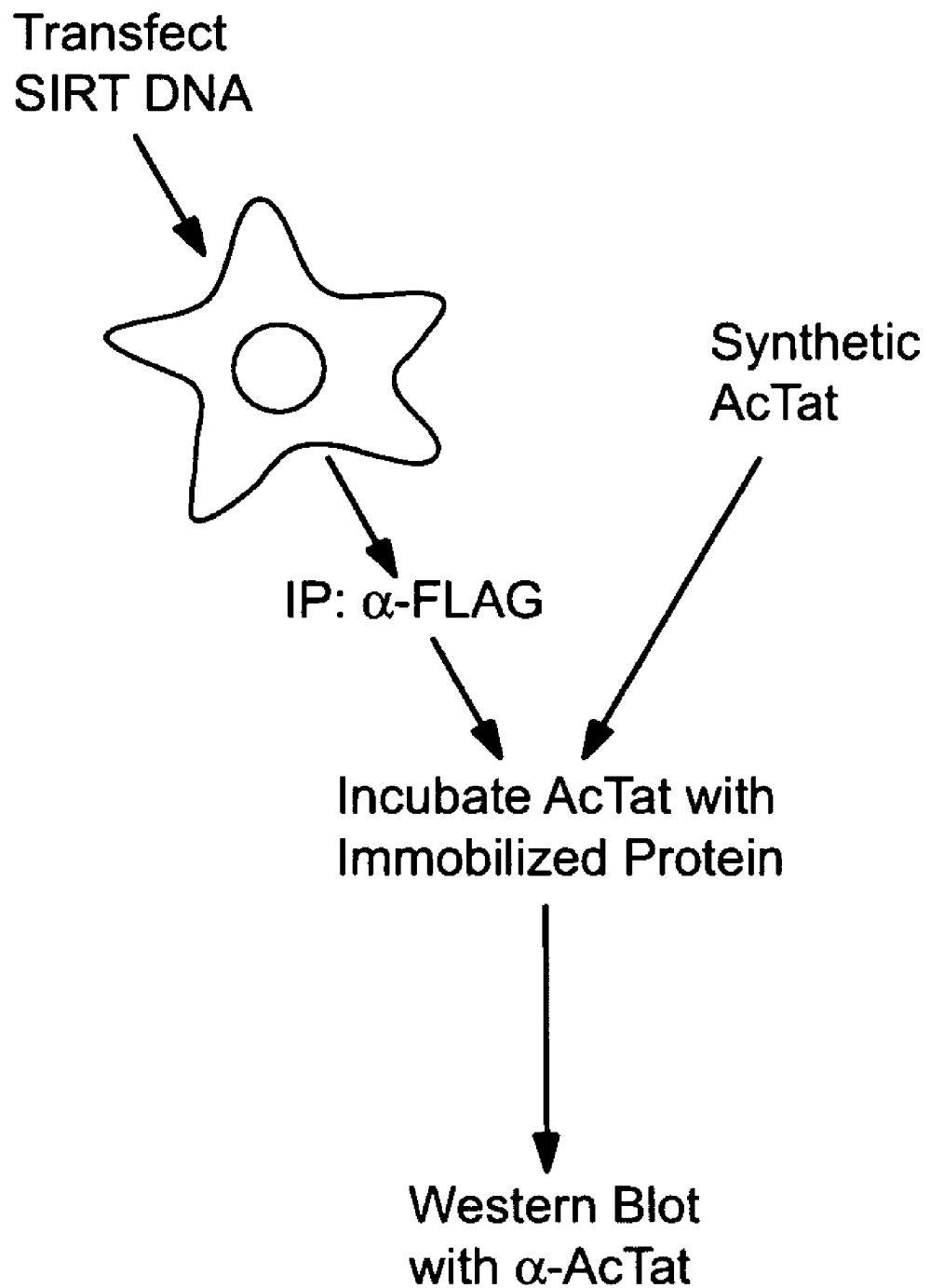
FIG. 1 is a schematic depiction of a Tat deacetylation assay with immunoprecipitated SIRT1-7 proteins.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of an HIV infection, the term "treatment" encompasses prevention of establishment of a systemic infection following initial contact with the virus; a reduction in one or more symptoms of AIDS; an increase in CD4+ T lymphocyte counts; a reduction in viral load; and prophylactic treatment of an individual not yet infected with the virus.

The term "effective amount" or "therapeutically effective amount" as used herein refers to a dosage sufficient to provide for treatment for the disease state being treated or to otherwise provide the desired effect (e.g., reduction of viral load; increase in CD4+ T cell count; etc.). The precise dosage will vary according to a variety of factors such as subject-dependent variables (e.g., age, immune system health, etc.), the disease (e.g., the particular immunodeficiency virus), and the treatment being effected. In the case of an immunodeficiency virus, an "effective amount" is that amount necessary to substantially improve the likelihood of treating the infection, in particular that amount which improves the likelihood of successfully preventing systemic infection or eliminating infection when it has occurred.

The terms "individual," "host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by an immunodeficiency virus.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; removal of cells; removal of certain cell types; or enrichment for certain cell populations, such as CD4+ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like. The term "biological sample" includes bodily fluids, including, but not limited to, blood, serum, plasma, urine, bronchoalveolar lavage, sputum, and the like.

The term "immunodeficiency virus" as used herein, refers to human immunodeficiency virus-1 (HIV-1); human immunodeficiency virus-2 (HIV-2); any of a variety of HIV subtypes and quasispecies; simian immunodeficiency virus (SUV); and feline immunodeficiency virus (FIV).

The term "isolated compound" means a compound which has been substantially separated from, or enriched relative to, other compounds with which it occurs in nature. Isolated compounds are usually at least about 80%, more usually at least 90% pure, even more preferably at least 98% pure, most preferably at least about 99% pure, by weight. The present invention is meant to comprehend diastereomers as well as their racemic and resolved, enantiomerically pure forms and pharmaceutically acceptable salts thereof.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound (e.g., compound of Formula I) employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, e.g., using a penetration enhancer. In other embodiments, the pharmaceutical compositions are suitable for administration by a route other than transdermal administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl, aryl, heteroaryl, aralkyl, heteroaralkyl, cycloalkyl or heterocyclyl.

A "pharmaceutically acceptable enol ester" of a compound of the invention means an enol ester that is pharmaceutically acceptable and that possesses the desired pharmacological activity of the parent compound, and includes, but is not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Pro-drugs" means any compound that releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorom-ethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl)carboxamide, protected N-($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4- bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl) n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic. Chemistry", 4th edition J. March, John Wiley and Sons, New York, 1992).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an acetylated Tat polypeptide" includes a plurality of such polypeptides and reference to "a selective SIRT1 inhibitor" includes reference to one or more selective SIRT1 inhibitors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides treatment methods involving modulating a sirtuin activity and/or a sirtuin mRNA and/or a sirtuin polypeptide level. The sirtuin is in some embodiments a SIRT1. The sirtuin is in other embodiments a SIRT2. The sirtuin is in other embodiments a SIRT3. The present invention provides treatment methods involving modulating a SIRT1 activity and/or a SIRT1 mRNA and/or polypeptide level. The present invention provides methods of inhibiting SIRT1 Tat deacetylase activity. Methods of inhibiting sirtuins are useful for inhibiting immunodeficiency virus infections. For example, methods of inhibiting SIRT1 Tat deacetylase activity are useful for treating immunodeficiency virus infections, particularly human immunodeficiency virus (HIV) infection. Thus, the present invention provides methods of treating an immunodeficiency virus infection, generally involving inhibiting SIRT1 Tat deacetylase activity. The present invention further provides methods of identifying agents that modulate sirtuin activity (e.g., SIRT1 activity), particularly ability of sirtuins to interact with (e.g., bind and/or deacetylate) a substrate, e.g., a viral substrate such as a Tat polypeptide. The present invention further provides active agents that modulate sirtuin activity or expression; and compositions, including pharmaceutical compositions, comprising the active agents.

The present invention provides compositions comprising agents that inhibit SIRT1 deacetylase activity, particularly SIRT1 Tat deacetylase activity. The compositions are useful to inhibit immunodeficiency virus replication, particularly human immunodeficiency virus (HIV) replication. Thus, the compositions are useful to treat an HIV infection in an individual in need thereof.

The present invention is based in part on the observation that SIRT1 (sirtuin; silent mating type information regulation 2 homolog), a class III human deacetylase, deacetylates Tat. Tat regulates HIV transcription and is itself regulated by reversible acetylation. Deacetylation of Tat by SIRT1 is required for Tat transactivation. SIRT1 is thus a target for therapeutic intervention in the treatment of HIV infection. Inhibition of SIRT1 Tat deacetylase activity inhibits HIV transcription, and thus inhibits the formation of HIV virions.

The present invention provides advantages over current drug treatments for HIV that target an HIV-encoded protein. Use of drugs that target an HIV-encoded protein is frequently accompanied by the emergence of drug-resistant HIV variants. Because the instant treatment methods target a cellular protein, rather than an HIV-encoded protein, the likelihood of developing drug resistance is low. A further advantage of a subject treatment method is that cells that are already infected with HIV can be treated.

Screening Methods

The present invention further provides methods of identifying agents that modulate sirtuin activity (e.g., SIRT1 activity), particularly ability of sirtuins to interact with (e.g., bind and/or deacetylate) a substrate, e.g., a viral substrate such as a Tat polypeptide. The methods generally involve contacting a sample containing a sirtuin (e.g., a SIRT1 protein, a SIRT2 protein, or a SIRT3 protein) and an acetylated Tat polypeptide with a test agent; and determining the effect, if any of the test agent on a sirtuin Tat deacetylase activity. A test agent that affects sirtuin deacetylase activity is a candidate agent for treating immunodeficiency virus infections.

The subject screening methods are carried out in vitro. In some embodiments, the methods are cell-based methods. In other embodiments, the methods are cell-free methods.

The terms "candidate agent," "agent", "substance," "test agent," and "compound" are used interchangeably herein. Candidate agents encompass numerous chemical classes, and are generally synthetic, semi-synthetic, or naturally-occurring inorganic or organic molecules. Candidate agents may be small organic compounds having a molecular weight of more than about 50 daltons and less than about 10,000 daltons, and in some embodiments between about 50 daltons and about 5,000 daltons, or between about 50 daltons and about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible. Where a candidate agent is part of a library, a subject screening method may be repeated a number of times to screen a plurality of compounds from a library.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity are considered candidate agents.

Assays of the invention usually include one or more controls. Thus, a test sample includes a test agent, and a control sample has all the components of the test sample except for the test agent. Generally a plurality of assay mixtures is run in parallel with different agent concentrations to obtain a differential response to the various concentrations. Typically, one of these concentrations serves as a negative control, i.e. at zero concentration or below the level of detection. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as nuclease inhibitors, anti-microbial agents, etc. may be used. The components may be added in any order. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

The screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times.

In many embodiments, a subject method of identifying an agent that modulates a Tat deacetylase activity will include a control for an effect of an agent on a deacetylase activity other than Tat deacetylase activity. For example, in some embodiments, a subject screening method will in some embodiments include a control substrate such as acetylated p53. A suitable candidate agent is one that selectively inhibits Tat deacetylase activity, e.g., does not substantially inhibit deacetylation of acetylated substrates other than Tat.

In some embodiments, the present invention provides methods of identifying an agent that inhibits a SIRT1 Tat deacetylase activity. The methods generally involve contacting a sample containing a SIRT1 protein and an acetylated Tat polypeptide with a test agent; and determining the effect, if any, of the test agent on a SIRT1 Tat deacetylase activity. A test agent that affects SIRT1 deacetylase activity is a candidate agent for treating immunodeficiency virus infections.

In some embodiments, a subject method is an in vitro cell-based method that involves contacting a cell that produces a SIRT1 polypeptide (or an active SIRT1 polypeptide fragment) and a Tat polypeptide with a test agent; and determining the effect, if any, of the test agent on the acetylation state of the Tat polypeptide in the cell. Determining the effect of the test agent on the acetylation state of the Tat polypeptide in the cell will in some embodiments comprise determining the level of acetylated Tat polypeptide in the cell.

In some embodiments, the present invention provides methods of identifying an agent that inhibits a SIRT2 Tat deacetylase activity. The methods generally involve contacting a sample containing a SIRT2 protein and an acetylated Tat polypeptide with a test agent; and determining the effect, if any, of the test agent on a SIRT2 Tat deacetylase activity. A test agent that affects SIRT2 deacetylase activity is a candidate agent for treating immunodeficiency virus infections.

In some embodiments, the present invention provides methods of identifying an agent that inhibits a SIRT3 Tat deacetylase activity. The methods generally involve contacting a sample containing a SIRT3 protein and an acetylated Tat polypeptide with a test agent; and determining the effect, if any, of the test agent on a SIRT3 Tat deacetylase activity. A test agent that affects SIRT3 deacetylase activity is a candidate agent for treating immunodeficiency virus infections.

A test agent of interest is one that reduces sirtuin (e.g., SIRT1, SIRT2, or SIRT3) Tat deacetylase activity by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to the level of sirtuin (e.g., SIRT1, SIRT2, or SIRT3) Tat deacetylase activity in a control in the absence of the test agent.

In general, a subject assay for identifying agents that inhibit SIRT1 Tat deacetylase activity involves contacting a SIRT1 polypeptide and an acetylated Tat polypeptide substrate in the presence of a test agent; and determining the effect, if any, of the test agent on SIRT1 Tat deacetylase activity. In some embodiments, the assay is a cell-free in vitro assay. In other embodiments, the assay is a cell-based in vitro assay.

In some embodiments, the assay is a cell-free in vitro assay. In these embodiments, an isolated SIRT1 polypeptide, an isolated acetylated Tat polypeptide substrate, nicotinamide adenine dinucleotide (NAD$^+$) are combined with a test agent, to form a test sample. The effect, if any, of the test agent on SIRT1 Tat deacetylase activity is determined. The SIRT1 protein is in many embodiments free of other proteins, and in particular free of other deacetylases. In these embodiments, the SIRT1 polypeptide and the acetylated Tat polypeptide represent at least 10% by weight of the proteins in the sample, e.g., the SIRT1 polypeptide and the acetylated Tat polypeptide represent at least 10%, at least 20%, at least 25%, at least 30%, at least 35%, at least 40%, at least 45%, at least 50%, at least 55%, at least 60%, at least 70%, at least 75%, at least 80%, at least 90%, or at least 95%, or more by weight of the proteins in the sample.

In other embodiments, the assay is a cell-based in vitro assay. In these embodiments, cells that synthesize both SIRT1 and Tat are contacted with a test agent; and the effect, if any of the test agent on SIRT1 Tat deacetylase activity is determined. Cells that are suitable for use include any eukaryotic cell (e.g., a mammalian cell, a yeast cell, an insect cell, an amphibian cell, and the like), which eukaryotic cell can be a primary cell, but will in many embodiments be a cell line. Suitable mammalian cell lines include, but are not limited to, CHO cells, NIH 3T3 cells, H9 cells, and the like. In some embodiments, the cell is one that produces SIRT1 endogenously. In other embodiments, the cell is genetically modified with a polynucleotide that comprises a nucleotide sequence that encodes a SIRT1 polypeptide. In general, the cell is genetically modified with a polynucleotide that comprises a nucleotide sequence that encodes a Tat polypeptide.

In some embodiments, a subject screening method is an in vitro cell-based method wherein the cell that produces the sirtuin (e.g., SIRT1, SIRT2, SIRT3) is a cell that is genetically modified to produce the sirtuin. Thus, e.g., an expression construct is introduced into the cell, where the expression construct comprises a nucleotide sequence that encodes a SIRT1 polypeptide (or a SIRT2 polypeptide, or a SIRT3 polypeptide), and where the SIRT1-encoding nucleotide sequence is operably linked to one or more control elements (e.g., promoters) that provide for expression of the SIRT1-encoding nucleotide sequence and production of the SIRT1 protein in the cell. In some embodiments, a subject screening method is an in vitro cell-based method wherein the cell that produces a Tat polypeptide is a cell that is genetically modified to produce the Tat polypeptide. Thus, e.g., an expression construct is introduced into the cell, where the expression construct comprises a nucleotide sequence that encodes a Tat polypeptide, and where the Tat-encoding nucleotide sequence is operably linked to one or more control elements (e.g., promoters) that provide for expression of the Tat-encoding nucleotide sequence and production of the Tat protein in the cell. In some embodiments, the cell is genetically modified to produce both the SIRT1 protein and the Tat protein. Thus, in some embodiments, the SIRT1 polypeptide, the Tat polypeptide, or both the SIRT1 polypeptide and the Tat polypeptide are produced recombinantly in the cell.

Sirtuins

Suitable sirtuins include SIRT1, SIRT2, and SIRT3 polypeptides. SIRT1, SIRT2, and SIRT3 polypeptides are known in the art. SIRT1, SIRT2, and SIRT3 mRNA sequences, as well as cDNA sequences encoding SIRT1, SIRT2, and SIRT3 polypeptides are known in the art.

SIRT1 polypeptides that are suitable for use in a subject assay include human SIRT1 polypeptides; murine SIRT1 polypeptides; variants of a human SIRT1 or mouse SIRT1 polypeptides; enzymatically active fragments of a SIRT1 polypeptide; SIRT1 fusion proteins; and the like.

The amino acid sequences of several SIRT1 polypeptides are publicly available. See, e.g., GenBank Accession Nos. Q96EB6, AAH12499, NP_036370, and AAD40849 for human SIRT1 amino acid sequences; and GenBank Accession Nos. Q923E4 and NP_062786 for mouse SIRT1 amino acid sequences. SIRT1 polypeptides from other species can also be used.

SIRT2 polypeptides that are suitable for use in a subject assay include human SIRT2 polypeptides; murine SIRT2 polypeptides; variants of a human SIRT2 or mouse SIRT2 polypeptides; enzymatically active fragments of a SIRT2 polypeptide; SIRT1 fusion proteins; and the like.

The amino acid sequences of several SIRT2 polypeptides are publicly available. See, e.g., GenBank Accession Nos. NP_085096, NP_036369, AAH03547, and AAH03012 for human SIRT2 amino acid sequences; GenBank Accession Nos. AAH86545 and NP_001008369 for rat SIRT2 amino acid sequences; and GenBank Accession No. NP_071877 for a mouse SIRT2 amino acid sequence. SIRT2 polypeptides from other species can also be used.

SIRT3 polypeptides that are suitable for use in a subject assay include human SIRT3 polypeptides; murine SIRT3 polypeptides; variants of a human SIRT3 or mouse SIRT3 polypeptides; enzymatically active fragments of a SIRT3 polypeptide; SIRT3 fusion proteins; and the like.

The amino acid sequences of several SIRT3 polypeptides are publicly available. See, e.g., GenBank Accession Nos. NP_07878 and AAH25878 for mouse SIRT3 amino acid sequences; and NP_036371, AAH01042, and AAD40851 for human SIRT3 amino acid sequences. SIRT3 polypeptides from other species can also be used.

The SIRT1, SIRT2, and SIRT3 polypeptides to be used in the methods of the present invention may be any of natural SIRT1, SIRT2, and SIRT3 polypeptides, recombinant SIRT1, SIRT2, and SIRT3 polypeptides, and derivatives thereof so far as they have Tat deacetylase activity.

The amino acid sequence of the SIRT1, SIRT2, and SIRT3 polypeptides may be altered in various ways known in the art to generate targeted changes in sequence. A variant polypeptide will usually be substantially similar to the sequences provided herein, i.e., will differ by at least one amino acid, and may differ by one amino acid, two amino acids, three amino acids, four amino acids, or from about 5 amino acids to about 10 amino acids, but generally not more than about ten amino acids, not more than about 15 amino acids, or not more than about 20 amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

A sirtuin polypeptide may be modified in various ways, as long as the polypeptide retains Tat deacetylase activity. Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g., those made by modifying the glycosylation patterns of a polypeptide during its synthesis and processing or in further processing steps; e.g., by exposing the polypeptide to enzymes that affect glycosylation, such as mammalian glycosylating or deglycosylating enzymes. Also embraced are sequences that have phosphorylated amino acid residues, e.g., phosphotyrosine, phosphosemme, or phosphothreonine.

Also suitable for use are enzymatically active SIRT1, SIRT2, and SIRT3 polypeptides that have been modified using ordinary chemical techniques so as to improve their resistance to proteolytic degradation, or to optimize solubility properties. Analogs may be used that include residues other than naturally occurring L-amino acids, e.g., D-amino acids or non-naturally occurring synthetic amino acids. The protein may be pegylated to enhance stability.

SIRT1, SIRT2, and SIRT3 polypeptides may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

SIRT1, SIRT2, and SIRT3 polypeptides may also be isolated and purified in accordance with conventional methods of recombinant synthesis. A lysate may be prepared of the expression host and the lysate purified using high performance liquid chromatography (HPLC), fast protein liquid chromatograph, size exclusion chromatography, gel electrophoresis (e.g., one-dimensional gel electrophoresis, two-dimensional gel electrophoresis), affinity chromatography, or other purification technique.

Tat Polypeptide Substrates

Tat substrates that are suitable for use in a subject screening method include a full-length acetylated Tat polypeptide; and an acetylated Tat polypeptide fragment. The term "acetylated Tat polypeptide" includes full-length acetylated Tat polypeptides, and acetylated Tat polypeptide fragments. Suitable acetylated Tat polypeptides include isolates of naturally-occurring Tat polypeptides; synthetic Tat polypeptides; and recombinantly produced Tat polypeptides. In some embodiments, an acetylated Tat polypeptide is coupled to an insoluble support, or a carrier. In some embodiments, an acetylated Tat polypeptide includes $K_{50}$, and at least one, two, three, four, or five amino acids on the carboxyl-terminal and/or the amino-terminal side of $K_{50}$.

A suitable acetylated Tat polypeptide includes all or a portion of any known Tat protein from any immunodeficiency virus, provided that the polypeptide comprises at least amino acid one acetylated lysine residue, and includes at least three, four, five, or more additional amino acids on the amino-terminal side of the acetylated lysine residue and three, four, five, or more additional amino acids on the carboxyl-terminal side of the acetylated lysine residue. Acetylated lysine residues include, but are not limited to, K28, K41, and K50. In some embodiments, a suitable acetylated Tat polypeptide includes one acetylated lysine residue. In other embodiments, a suitable acetylated Tat polypeptide includes two acetylated lysine residues. In other embodiments, a suitable acetylated Tat polypeptide includes three or more acetylated lysine residues.

In certain embodiments, a suitable acetylated Tat polypeptide comprises amino acid sequences corresponding to HIV-1. In many embodiments, a suitable acetylated Tat polypeptide comprises acetylated Lysine-50 (Ac-Lys50) and at least about three, four, five, or more additional amino acids on the amino-terminal side of amino acid 50 and three, four, five, or more additional amino acids on the carboxyl-terminal side of amino acid 50, where Lys50 is acetylated. In some embodiments, a suitable acetylated Tat polypeptide is acetylated on amino acid 50 (Lys).

A suitable acetylated Tat polypeptide is generally from about 7 to about 72 amino acids in length, e.g., from about 7 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 55 amino acids, from about 55 amino acids to about 60 amino acids, from about 60 amino acids to about 65 amino acids, or from about 65 amino acids to about 70 amino acids in length, up to the full-length Tat polypeptide.

In some embodiments, a suitable acetylated Tat polypeptide includes heterologous amino acid sequences, e.g., a subject acetylated Tat polypeptide may include a heterologous polypeptide. Heterologous polypeptides are polypeptides other than Tat, and include, but are not limited to, polypeptide carriers; immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, etc.), and the like; a "purification tag," e.g., polypeptides that facilitate purification or isolation of the fusion protein, e.g., metal ion binding polypeptides such as 6His tags (e.g., acetylated Tat/6His), glutathione-5-transferase (GST), and the like.

In some embodiments, a suitable acetylated Tat polypeptide is detectably labeled. Various labels include radioisotopes, fluorescers (e.g., fluorescent dyes), chemiluminescers, enzymes, specific binding molecules, particles, e.g. magnetic particles, and the like. Specific binding molecules include pairs, such as biotin and streptavidin, digoxin and antidigoxin etc.

In some embodiments, the Tat protein is physically associated with (detectably labeled with) a fluorophore. Suitable fluorophores include, but are not limited to, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1', 3,3'-tetraethylbenzimidazoylcarbocyanine iodide), tetrabromorhodamine 123, rhodamine 6G, TMRM (tetramethylrhodamine-, methyl ester), TMRE (tetramethylrhodamine, ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, and fluorescent europium and terbium complexes; and the like.

Numerous HIV Tat protein amino acid sequences are found under GenBank, and any of these publicly available sequences can be used in the present invention. Exemplary, non-limiting, HIV Tat protein amino acid sequences are found under GenBank Accession Nos. AAO26250, AAO26252, AAO26254, AAO26258, AAO26260, AAO26262, AAO26264, AAO26266, AAO26268, AAO26270, AAO26272, AAO26274, AAO26276, AAO26278, AAO26280, AAO26282, AAO26284, AAO26286, AAO26288, AAO26290, AAO26292, AAO26294, AAO26296, AAO26298, AAO26300, AAO26302, AAO26304, AAO26306, AAO26308; AAB50256; AAL12204; AAL12195; AAL12186; AAL12177; AAN47131; AAN47122; AAN47113; AAN47104; AAN03332; AAN03323; AAN03314; AAN03305; AAN03296; AAN03287; AAN03278; AAN31592; AAN64126; AAN64117; AAN64108; AAN64099; AAN64090; AAN64080; K02013; AAL29460; etc. Additional HIV Tat amino acid sequences are found in Peloponese et al. (1999) *J. Biol. Chem.* 274:11473-11478; and Goldstein (1996) *Nat. Med.* 2:960-964.

In some embodiments, an acetylated Tat polypeptide substrate comprises the following consensus sequence (where amino acid sequences are provided from amino-terminus (N-terminus) to carboxyl-terminus (C-terminus): Lys-(Ala or Gly)-Leu-Gly-Ile-Ser-Tyr-Gly-Arg-<u>Lys</u>-Lys-Arg-(Arg or Lys)-(Gln or His)-Arg-Arg-(Arg or Gly or Lys or Ser)-(Pro or Ala or Thr)-(Gln or Pro or Thr) (SEQ ID NO:1), wherein one or more of the lysines is acetylated. In some embodiments, the lysine corresponding to Lys-50 in the full-length protein is acetylated (e.g., the underlined Lys in SEQ ID NO:1). In a particular embodiment, an acetylated Tat polypeptide substrate, includes the amino acid sequence Ser-Tyr-Gly-Arg-AcLys-Lys-Lys-Arg-Arg-Gln-Arg (SEQ ID NO:2). Other useful substrates include polypeptides that include at least 5, 6, 7, or 8 contiguous amino acids of the amino acid sequence set forth in SEQ ID NO:2, particularly a fragment comprising the acetylated lysine (AcLys) and at least one amino acid, at least two amino acids, at least three amino acids, or at least four amino acids on the amino- and/or the carboxyl-terminal side of the acetylated lysine.

In some embodiments, a Tat polypeptide substrate includes one or more additional amino acids not found in a naturally-occurring Tat polypeptide. Such amino acids include amino acids added to the amino-terminus and/or the carboxyl-terminus of an acetylated Tat polypeptide. Amino acids added to a Tat polypeptide include amino acids that serve as linkers, e.g., to a carrier polypeptide or other polypeptide, as discussed above. Linking can be performed to any amino acid that contains an active group, including, but not limited to, amino acids with a free $NH_2$ group, e.g., lysine, arginine, asparagine, and glutamine; a free $NH_2$ group of an amino terminal amino acid; amino acids with sulfhydryl groups, e.g., cysteine, or an amino acid to which an $SH_2$ group has been chemically added; amino acids with carboxyl groups, e.g., aspartic acid, glutamic acid; and a COOH group of a carboxyl-terminal amino acid.

In some embodiments, a Tat polypeptide substrate includes an additional cysteine residue appended to the C-terminus. A cysteine residue serves as a linkage site for linking to a carrier.

In some embodiments, a Tat polypeptide substrate includes heterologous amino acid sequences, e.g., a Tat polypeptide substrate may include a heterologous polypeptide. Heterologous polypeptides are polypeptides other than Tat, and include, but are not limited to, immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, alkaline phosphatase, etc.), and the like; polypeptides that facilitate purification or isolation of the fusion protein, e.g., metal ion binding polypeptides such as 6His tags (e.g., acetylated Tat/6His), glutathione S-transferase (GST), and the like.

A Tat polypeptide may be synthesized chemically or enzymatically, may be produced recombinantly, may be isolated from a natural source, or a combination of the foregoing. A Tat polypeptide may be isolated from natural sources using standard methods of protein purification known in the art, including, but not limited to, high performance liquid chromatography, fast protein liquid chromatography, size exclusion chromatography, gel electrophoresis (one-dimensional, two-dimensional, etc.), affinity chromatography, or other purification technique. One may employ solid phase peptide synthesis techniques, where such techniques are known to those of skill in the art. See Jones, *The Chemical Synthesis of Peptides* (Clarendon Press, Oxford)(1994). Generally, in such methods a peptide is produced through the sequential additional of activated monomeric units to a solid phase bound growing peptide chain. Peptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co. (1984); Tam et al., J. Am. Chem. Soc. 105:6442 (1983); Merrifield, Science 232:341-347 (1986); and Barany and Merrifield, The Peptides, Gross and Meienhofer, eds., Academic Press, New York, pp. 1-284 (1979), each of which is incorporated herein by reference. Well-established recombinant DNA techniques can be employed for production of a Tat polypeptide, which can be acetylated during or after synthesis.

For production of a Tat polypeptide by recombinant means, the polynucleotide comprising a nucleotide sequence encoding Tat ("a Tat polynucleotide") is expressed in any convenient expression system, including, for example, bacterial, yeast, insect, amphibian and mammalian systems. Suitable vectors and host cells are described in U.S. Pat. No. 5,654, 173. In the expression vector, a Tat polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present.

Expression cassettes may be prepared comprising a transcription initiation region, the gene or fragment thereof, and a transcriptional termination region. After introduction of the expression cassette containing a Tat polynucleotide, the cells containing the construct may be, selected by means of a selectable marker, the cells expanded and then used for expression.

A Tat polypeptide can be acetylated in vitro, either after synthesis or during synthesis. For example, where a Tat polypeptide is prepared synthetically in vitro, a Tat polypeptide is acetylated in a solution comprising 50 mM HEPES, pH 8, 10% glycerol, 1 mM DTT, 10 mM sodium butyrate, and 20 nmol acetyl-coenzyme A (AcCoA) in the presence of an acetyl transferase for 2 hours at 30° C. See, e.g., Ott et al. (1999) *Curr. Biol.* 9:1489-1492. An acetylated Tat protein can be generated as described in, e.g., Dorr et al. (2002) *EMBO J* 21:2715-2723; or Peloponese (1999) *J. Biol. Chem.* 274: 11473-11478.

In other embodiments, a Tat polypeptide is acetylated by a living cell, e.g., the acetylated lysine is incorporated during synthesis of the Tat polypeptide. Acetylated Tat polypeptide synthesized by a living eukaryotic cell is recovered using standard methods for protein purification. In some embodiments, the Tat polypeptide that is acetylated by a living eukaryotic cell is a fusion protein comprising a moiety that facilitates purification (e.g., a binding moiety), e.g., GST, 6His, etc., and the acetylated Tat polypeptide is purified using a separation medium appropriate to the binding moiety.

Detecting SIRT1 Tat Deacetylase Activity

A variety of methods are available to evaluate interaction between a sirtuin (e.g., SIRT1) and a substrate (e.g., a Tat substrate). For example, the interaction can be evaluated by monitoring sirtuin enzymatic activity in an assay that includes an acetylated Tat substrate or by monitoring a binding interaction between a sirtuin and a Tat substrate (e.g., in the presence or absence of cofactors). In one exemplary enzymatic assay, following a suitable period of time, a test sample comprising SIRT1, a Tat substrate, NAD$^+$, and a test agent, is analyzed for SIRT1 Tat deacetylase activity. The effect of the test agent on SIRT1 Tat deacetylase activity is determined using any convenient method.

In one embodiment, the level of acetylated Tat in the sample is analyzed. A decrease in the level of Tat is a measure of SIRT1 activity. Methods of determining the level of acetylated Tat in a sample include immunological assays using antibody that is specific for acetylated form of Tat, and that therefore distinguishes between acetylated Tat and deacetylated Tat. Any of a variety of immunological assays can be used, including, e.g., enzyme linked immunosorbent assay (ELISA), radioimmunoassay (RIA), protein blot ("Western" blot) assays, and the like. In some embodiments, mass spectroscopy is used. Other means of assessing the level of acetylated Tat in a sample include nuclear magnetic resonance (NMR) methods.

Mass spectroscopic methods for distinguishing between acetylated Tat and deacetylated Tat are known in the art. Furia et al. (2002) *J. Biol. Chem.* 277:4973-4980. The term "mass spectrometry" is used herein in its usual sense to include various methods such as tandem mass spectrometry, matrix assisted laser desorption ionization (MALDI) time-of-flight (TOF) mass spectrometers (MS), MALDI-TOF-TOF MS, MALDI Quadrupole-time-of-flight (Q-TOF) MS, electrospray ionization (ESI)-TOF MS, ESI-Q-TOF, ESI-TOF-TOF, ESI-ion trap MS, ESI Triple quadrupole MS, ESI Fourier Transform Mass Spectrometry (FTMS), MALDI-FTMS, MALDI-Ion Trap-TOF, and ESI-Ion Trap TOF. These mass spectrometry methods are well known in the art, see e.g., Chapters 1-4 etc. of Gary Siuzdak, "Mass Spectrometry for Biotechnology," Academic Press, N.Y., (1996). At its most basic level, mass spectrometry involves ionizing a molecule and then measuring the mass of the resulting ion. Since molecules ionize in a way that is well known, the molecular weight of the molecule can generally be accurately determined from the mass of the ion.

Where the test agent inhibits SIRT1 Tat deacetylase activity, the level of acetylated Tat will be higher than the level of acetylated Tat in the absence of the test agent. Thus, a higher level of acetylated Tat, compared to the level of acetylated Tat in a control sample in the absence of the test agent, indicates that the test agent inhibits SIRT1 Tat deacetylase.

In another embodiment, SIRT1 activity can be determined by measuring the level of $NAD^+$ in the test sample. The action of SIRT1 on acetylated Tat can be coupled to a second enzymatic reaction that reduces $NAD^+$ to NADH, and measuring fluorescence of NADH at, e.g., 340 nm. Thus, in some embodiments, the determining step involves a second enzymatic reaction for determining the level of $NAD^+$ in the sample, using an enzyme that catalyzes the reduction of $NAD^+$ to NADH. The effect of the test agent on SIRT1 Tat deacetylase activity is determined by measuring the level of NADH. Where the agent inhibits SIRT1 Tat deacetylase activity, the level of $NAD^+$ in the sample will be greater than the level of $NAD^+$ in the sample in the absence of the test agent. Thus, where the agent inhibits SIRT1 Tat deacetylase activity, the level of NADH formed in the second enzymatic reaction in the determination step will be higher than the level of NADH in the absence of the test agent. Thus, a higher level of $NAD^+$ in the test sample, compared to the level of $NAD^+$ in a control sample in the absence of the test agent, indicates that the test agent inhibits SIRT1 Tat deacetylase activity.

Where the assay is a cell-based assay, determination of the effect, if any, of the test agent on SIRT1 Tat deacetylase activity is performed using any known method. For example, after a suitable period of time, cells are lysed, and the level of acetylated Tat in the cells is determined using thin layer chromatography.

As another non-limiting example, radioactively labeled NAD is used in the reaction, and the level of radioactive nicotinamide that is formed is detected as a readout for SIRT1 Tat deacetylase activity.

Agents that Inhibit Sirtuin Activity

The present invention further provides active agents that reduce or inhibit Tat deacetylase activity, as well as agents that modulate sirtuin (e.g., SIRT1, SIRT2, SIRT2) expression, localization, activity, and availability in cells; and compositions, including pharmaceutical compositions, comprising the agents. In some embodiments, an active agent is an agent identified using a screening method of the invention. The subject agents are useful for inhibiting immunodeficiency virus replication, and are therefore useful for treating immunodeficiency virus infections. Suitable agents include small molecule inhibitors; peptide inhibitors; siRNA; antisense RNA; ribozymes; intrabodies; and the like.

In many embodiments, an agent that inhibits SIRT1 Tat deacetylase that is suitable for use in a subject treatment method is an agent that inhibits SIRT1 Tat deacetylase activity by at least about 10%, at least about 15%, at least about 20%, at least about 25%, at least about 30%, at least about 40%, at least about 50%, at least about 60%, at least about 70%, at least about 80%, or at least about 90%, or more, compared to the SIRT1 Tat deacetylase activity in the absence of the compound.

In many embodiments, an agent that inhibits SIRT2 Tat deacetylase that is suitable for use in a subject treatment method is an agent that inhibits SIRT2 Tat deacetylase activity by at least about 10%, at least about 15%, at least about 20%, at least about 25%, at least about 30%, at least about 40%, at least about 50%, at least about 60%, at least about 70%, at least about 80%, or at least about 90%, or more, compared to the SIRT2 Tat deacetylase activity in the absence of the compound.

In many embodiments, an agent that inhibits SIRT3 Tat deacetylase that is suitable for use in a subject treatment method is an agent that inhibits SIRT3 Tat deacetylase activity by at least about 10%, at least about 15%, at least about 20%, at least about 25%, at least about 30%, at least about 40%, at least about 50%, at least about 60%, at least about 70%, at least about 80%, or at least about 90%, or more, compared to the SIRT3 Tat deacetylase activity in the absence of the compound.

In some embodiments, an agent that is suitable for use in a subject treatment method inhibits SIRT1 and SIRT2, but does not substantially inhibit other enzymes, e.g., at the $IC_{50}$ for SIRT1, the agent inhibits SIRT2, but does not result in more than about 5%, more than about 10%, or more than about 25% inhibition of any other enzyme, e.g., SIRT3, or SIRT4.

In some embodiments, an agent that is suitable for use in a subject treatment method inhibits SIRT1 and SIRT3, but does not substantially inhibit other enzymes, e.g., at the $IC_{50}$ for SIRT1, the agent inhibits SIRT3, but does not result in more than about 5%, more than about 10%, or more than about 25% inhibition of any other enzyme, e.g., SIRT2, or SIRT4.

In some embodiments, an agent that is suitable for use in a subject treatment method inhibits SIRT1, SIRT2, and SIRT3, but does not substantially inhibit other enzymes, e.g., at the $IC_{50}$ for SIRT1, the agent inhibits SIRT2, and SIRT3, but does not result in more than about 5%, more than about 10%, or more than about 25% inhibition of any other enzyme, e.g., SIRT4.

In other embodiments, an agent that inhibits SIRT1 Tat deacetylase that is suitable for use in a subject treatment method is a selective inhibitor of SIRT1 Tat deacetylase. An agent that is a selective inhibitor of SIRT1 Tat deacetylase activity is an agent that does not substantially inhibit other enzymes, including, e.g., SIRT2 or SIRT3, e.g., at the $IC_{50}$ for SIRT1, the agent does not result in more than about 5%, more than about 10%, or more than about 25% inhibition of SIRT2 or SIRT3 enzymatic activity.

The term "selective inhibitor of SIRT1 Tat deacetylase" is used herein to mean compound which selectively inhibits SIRT1 Tat deacetylase activity in preference to SIRT2 (or any other enzyme) and particularly a compound for which the ratio of the $IC_{50}$ concentration (concentration inhibiting 50% of activity) for SIRT1 Tat deacetylase to the $IC_{50}$ concentration for SIRT2 is greater than 1. Such ratio is readily determined by assaying for SIRT1 Tat deacetylase activity and assaying for SIRT2 activity and from the resulting data obtaining a ratio of $IC_{50}$s.

Agents that inhibit SIRT1 Tat deacetylase activity and that are suitable for use in a subject treatment method inhibit SIRT1 Tat deacetylase activity with an $IC_{50}$ of less than about 100 μM, e.g., a suitable agent inhibits SIRT1 Tat deacetylase activity with an $IC_{50}$ of less than about 100 μM, less than about 90 μM, less than about 75 μM, less than about 50 μM, less than about 40 μM, less than about 25 μM, less than about 10 μM, less than about 1 μM, less than about 100 nM, less than about 80 nM, less than about 60 nM, less than about 50 nM, less than about 25 nM, less than about 10 nM, or less than about 1 nM, or less.

Agents that inhibit SIRT2 Tat deacetylase activity and that are suitable for use in a subject treatment method inhibit SIRT2 Tat deacetylase activity with an $IC_{50}$ of less than about 100 μM, e.g., a suitable agent inhibits SIRT2 Tat deacetylase activity with an $IC_{50}$ of less than about 100 μM, less than about 90 μM, less than about 75 μM, less than about 50 μM, less than about 40 μM, less than about 25 μM, less than about 10 μM, less than about 1 μM, less than about 100 nM, less than about 80 nM, less than about 60 nM, less than about 50 nM, less than about 25 nM, less than about 10 nM, or less than about 1 nM, or less.

Agents that inhibit SIRT3 Tat deacetylase activity and that are suitable for use in a subject treatment method inhibit SIRT3 Tat deacetylase activity with an $IC_{50}$ of less than about 100 μM, e.g., a suitable agent inhibits SIRT3 Tat deacetylase activity with an $IC_{50}$ of less than about 100 μM, less than about 90 μM, less than about 75 μM, less than about 50 μM, less than about 40 μM, less than about 25 μM, less than about 10 μM, less than about 1 μM, less than about 100 nM, less than about 80 nM, less than about 60 nM, less than about 50 nM, less than about 25 nM, less than about 10 nM, or less than about 1 nM, or less.

Small Molecule Inhibitors

In many embodiments, the SIRT1 inhibitor agent is a small molecule, e.g., a small organic or inorganic compound having a molecular weight of more than about 50 daltons and less than about 20,000 daltons, e.g., from about 50 daltons to about 100 daltons, from about 100 daltons to about 200 daltons, from about 200 daltons to about 500 daltons, from about 500 daltons to about 1000 daltons, from about 1000 daltons to about 2500 daltons, from about 2500 daltons to about 5000 daltons, from about 5000 daltons to about 7,500 daltons, from about 7,500 daltons to about 10,000 daltons, from about 10,000 daltons to about 15,000 daltons, or from about 15,000 daltons to about 20,000 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

In some embodiments, a suitable small molecule inhibitor is nicotinamide. In some embodiments, a suitable small molecule inhibitor is a structural analog or derivative of nicotinamide. In particular embodiments, a suitable structural analog or derivative of nicotinamide is one that is a selective SIRT1 inhibitor, and that has an $IC_{50}$ of less than about 100 μM, less than about 75 μM, less than about 50 μM, less than about 25 μM, less than about 10 μM, less than about 1 μM, less than about 100 nM, less than about 80 nM, less than about 60 nM, less than about 50 nM, less than about 25 nM, less than about 10 nM, or less than about 1 nM, or less.

In other embodiments, a small molecule inhibitor is a suramin analog such as NF279, NF023, and the like. NF023 is (8,8'-[carbonylbis(imino-3,1-phenylenecarbonylimino)]bis-1,3,5-naphthalene-trisulphonic acid); NF279 is (8,8'-[carbonylbis (imino-4,1-phenylenecarbonylimino-4,1-phenylenecarbonylimino)]bis-1,3,5-naphthalene-trisulphonic acid). In particular embodiments, a suitable structural analog or derivative of suramin analog is one that is a selective SIRT1 inhibitor, and that has an $IC_{50}$ of less than about 100 μM, less than about 75 μM, less than about 50 μM, less than about 25 μM, less than about 10 μM, less than about 1 μM, less than about 100 nM, less than about 80 nM, less than about 60 nM, less than about 50 nM, less than about 25 nM, less than about 10 nM, or less than about 1 nM, or less.

In some embodiments, a small molecule inhibitor has the structure of a splitomycin analog or derivative. In particular embodiments, a suitable splitomycin analog or derivative is one that is a selective SIRT1 inhibitor, and that has an $IC_{50}$ of less than about 100 μM, less than about 75 μM, less than about 50 μM, less than about 25 μM, less than about 10 μM, less than about 1 μM, less than about 100 nM, less than about 80 nM, less than about 60 nM, less than about 50 nM, less than about 25 nM, less than about 10 nM, or less than about 1 nM, or less.

In some embodiments, a suitable SIRT1 inhibitor is a compound of Formula I:

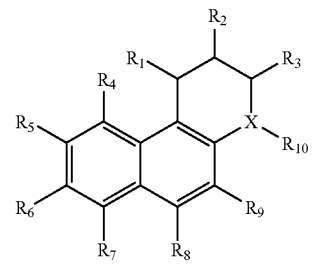

where X is C, O, N, or S;

where each of $R_6$, $R_7$, and $R_8$ is independently selected from a substituted or unsubstituted phenyl group; a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; an ether group, such as a methoxyl group; and an ethoxyl group;

where each of $R_1$, $R_3$, and $R_4$-$R_{10}$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; or an ether group, such as a methoxyl group or an ethoxyl group; a substituted or unsubstituted phenyl group; and a substituted or unsubstituted heteroaromatic group.

In some embodiments, a suitable SIRT1 inhibitor is a compound of Formula Ia:

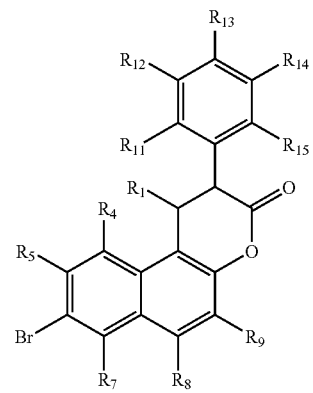

where each of $R_1$, $R_4$, $R_5$, and $R_7$-$R_{15}$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; or an ether group, such as a methoxyl group or an ethoxyl group; a substituted or unsubstituted phenyl group; and a substituted or unsubstituted heteroaromatic group.

In some embodiments, a suitable SIRT1 inhibitor is a compound of Formula Ib:

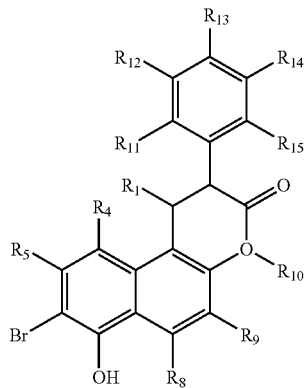

where each of $R_1$, $R_4$, $R_5$, and $R_8$-$R_{15}$ is independently selected from H; a halo (e.g., bromo, fluoro, chloro); a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; or an ether group, such as a methoxyl group or an ethoxyl group; a substituted or unsubstituted phenyl group; and a substituted or unsubstituted heteroaromatic group.

Figure 7B:
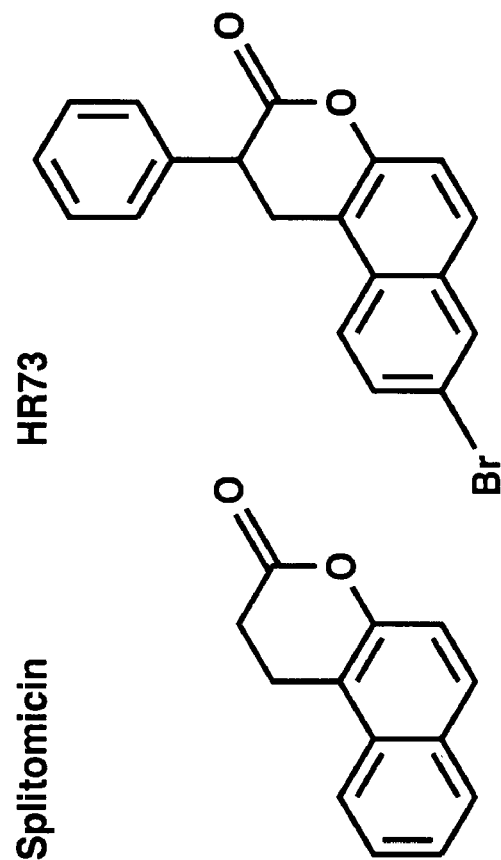
FIGS. 7A-7D depict inhibition of HIV gene expression by a small molecule inhibitor of SIRT1.

In some embodiments, a suitable compound is a compound identified as HR73 in FIG. 7B, where the structure is shown in FIG. 7B, and analogs and derivatives thereof, in particular, analogs and derivatives that are SIRT1 selective inhibitors.

Peptide Inhibitors

In some embodiments, an active agent is a peptide. Suitable peptides include peptides of from about 3 amino acids to about 50, from about 5 to about 30, or from about 10 to about 25 amino acids in length.

Peptides can include naturally-occurring and non-naturally occurring amino acids. Peptides may comprise D-amino acids, a combination of D- and L-amino acids, and various "designer" amino acids (e.g., Nβ-methyl amino acids, Cα-methyl amino acids, and Nα-methyl amino acids, etc.) to convey special properties to peptides. Additionally, peptide may be a cyclic peptide. Peptides may include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics may be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tretrazol; and the like.

A peptide may be a depsipeptide, which may be a linear or a cyclic depsipeptide. Kuisle et al. (1999) *Tet. Letters* 40:1203-1206. "Depsipeptides" are compounds containing a sequence of at least two alpha-amino acids and at least one alpha-hydroxy carboxylic acid, which are bound through at least one normal peptide link and ester links, derived from the hydroxy carboxylic acids, where "linear depsipeptides" may comprise rings formed through S—S bridges, or through an hydroxy or a mercapto group of an hydroxy-, or mercapto-amino acid and the carboxyl group of another amino- or hydroxy-acid but do not comprise rings formed only through peptide or ester links derived from hydroxy carboxylic acids. "Cyclic depsipeptides" are peptides containing at least one ring formed only through peptide or ester links, derived from hydroxy carboxylic acids.

Peptides may be cyclic or bicyclic. For example, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Methods for making cyclic peptides are well known in the art.

The term "bicyclic" refers to a peptide in which there exists two ring closures. The ring closures are formed by covalent linkages between amino acids in the peptide. A covalent linkage between two nonadjacent amino acids constitutes a ring closure, as does a second covalent linkage between a pair of adjacent amino acids which are already linked by a covalent peptide linkage. The covalent linkages forming the ring closures may be amide linkages, i.e., the linkage formed between a free amino on one amino acid and a free carboxyl of a second amino acid, or linkages formed between the side chains or "R" groups of amino acids in the peptides. Thus, bicyclic peptides may be "true" bicyclic peptides, i.e., peptides cyclized by the formation of a peptide bond between the N-terminus and the C-terminus of the peptide, or they may be "depsi-bicyclic" peptides, i.e., peptides in which the terminal amino acids are covalently linked through their side chain moieties.

A desamino or descarboxy residue can be incorporated at the terminii of the peptide, so that there is no terminal amino or carboxyl group, to decrease susceptibility to proteases or to restrict the conformation of the peptide. C-terminal functional groups include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, a peptide or peptidomimetic can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S., Bioconjugate Chem., 6:150-165 (1995); Monfardini, C, et al., Bioconjugate Chem., 6:62-69 (1995); U.S. Pat. Nos. 4,640,835; 4,496,689; 4,301,144; 4,670,417; 4,791,192; 4,179,337 or WO 95/34326.

Peptide inhibitors of SIRT1 activity will in some embodiments be conjugated to decapeptides comprised of Arginine residues to allow uptake across the plasma membrane by protein transduction. Such modifications allow peptides to enter cells (e.g., cross the plasma membrane) with high efficiency.

Another suitable agent for reducing an activity of SIRT1 is a peptide aptamer. Peptide aptamers are peptides or small polypeptides that act as dominant inhibitors of protein function. Peptide aptamers specifically bind to target proteins, blocking their function ability. Kolonin and Finley, PNAS (1998) 95:14266-14271. Due to the highly selective nature of peptide aptamers, they may be used not only to target a specific protein, but also to target specific functions of a given protein (e.g. a protein binding function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. Peptide aptamers can be isolated from random peptide libraries by yeast two-hybrid screens (Xu et al., PNAS (1997) 94:12473-12478). They can also be isolated from phage libraries (Hoogenboom et al., Immunotechnology (1998) 4:1-20) or chemically generated peptides/libraries.

Intrabodies

Intracellularly expressed antibodies, or intrabodies, are single-chain antibody molecules designed to specifically bind and inactivate target molecules inside cells. Intrabodies have been used in cell assays and in whole organisms. Chen et al., Hum. Gen. Ther. (1994) 5:595-601; Hassanzadeh et al., Febs Lett. (1998) 16(1, 2):75-80 and 81-86. Inducible expression vectors can be constructed with intrabodies that react specifically with SIRT1 protein.

Antisense, siRNAs, and Ribozymes

In some embodiments, the active agent is an agent that modulates, and generally decreases or down regulates, the expression of the gene encoding SIRT1 in the host. Such agents include, but are not limited to, antisense RNA, interfering RNA (including short interfering RNA; "siRNA"), ribozymes, and the like.

In some embodiments, the active agent is an interfering RNA (RNAi). RNAi includes double-stranded RNA interference (dsRNAi). Use of RNAi to reduce a level of a particular mRNA and/or protein is based on the interfering properties of double-stranded RNA derived from the coding regions of gene. In one example of this method, complementary sense and antisense RNAs derived from a substantial portion of the SIRT1 gene are synthesized in vitro. The resulting sense and antisense RNAs are annealed in an injection buffer, and the double-stranded RNA injected or otherwise introduced into the subject (such as in their food or by soaking in the buffer containing the RNA). See, e.g., WO99/32619. In another embodiment, dsRNA derived from an SIRT1 gene is generated in vivo by simultaneous expression of both sense and antisense RNA from appropriately positioned promoters operably linked to SIRT1 coding sequences in both sense and antisense orientations.

One approach well known in the art is short interfering RNA (siRNA) mediated gene silencing where expression products of an SIRT1 gene are targeted by specific double stranded SIRT1-derived siRNA nucleotide sequences that are complementary to at least a 19-25 nt long segment (e.g., a 20-21 nucleotide sequence) of the SIRT1 gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858 for descriptions of siRNA technology.

Antisense molecules can be used to down-regulate expression of the gene encoding SIRT1 in cells. Antisense compounds include ribozymes, external guide sequence (EGS) oligonucleotides (oligozymes), and other short catalytic RNAs or catalytic oligonucleotides which hybridize to the target nucleic acid and modulate its expression.

The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1996), supra.) Preferred oligonucleotides are chemically modified from the native phosphodiester structure, in order to increase their intracellular stability and binding affinity. A number of such modifications have been described in the literature, which modifications alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroanidate. Peptide nucleic acids replace the entire ribose phosphodiester backbone with a peptide linkage. Sugar modifications are also used to enhance stability and affinity. The β-anomer of deoxyribose may be used, where the base is inverted with respect to the natural α-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Exemplary modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Oligonucleotides having a morpholino backbone structure (Summerton, J. E. and Weller D. D., U.S. Pat. No. 5,034,506) or a peptide nucleic acid (PNA) backbone (P. E. Nielson, M. Egholm, R. H. Berg, O. Buchardt, Science 1991, 254: 1497) can also be used. Morpholino antisense oligonucleotides are amply described in the literature. See, e.g., Partridge et al. (1996) *Antisense Nucl. Acid Drug Dev.* 6:169-175; and Summerton (1999) *Biochem. Biophys. Acta* 1489:141-158.

Anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense oligodeoxynucleotides with a metal complex, e.g. terpyridylCu(II), capable of mediating mRNA hydrolysis are described in Bashkin et al. (1995), *Appl. Biochem. Biotechnol.* 54:43-56.

Formulations, Dosages, and Routes of Administration

As noted above, the instant invention provides compositions, including pharmaceutical compositions, comprising a sirtuin modulating agent. In some embodiments, the instant invention provides compositions, including pharmaceutical compositions, comprising a selective SIRT1 Tat deacetylase inhibitor. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

In general, an active agent (e.g., an agent that inhibits SIRT1 Tat deacetylase activity) is prepared in a pharmaceutically acceptable composition for delivery to a host. The terms "active agent," "drug," "agent," "therapeutic agent," and the like are used interchangeably herein. Pharmaceutically acceptable carriers preferred for use with an active agent (an agent that inhibits SIRT1 Tat deacetylase activity) may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an agent that inhibits SIRT1 Tat deacetylase activity may also be lyophilized using means well known in the art, for subsequent reconstitution and use according to the invention.

The present invention further provides a method of providing a pharmaceutical formulation for the treatment of a retroviral (e.g., an HIV) disorder in an individual in need thereof, the method generally involving:

i) evaluating a batch of an agent that modulates Tat deacetylase activity by testing a sample from the batch using an in vitro cell-based or an in vitro cell-free assay for Tat deacetylation, as described above; and ii) formulating material from the batch as a pharmaceutical composition.

In some embodiments, the method further involves administering the pharmaceutical composition to a subject having or suspected of having a retroviral disorder.

Formulations

An active agent (e.g., an agent that inhibits a SIRT1 Tat deacetylase activity) is administered to an individual in need thereof in a formulation with a pharmaceutically acceptable excipient(s).

In the subject methods, the active agent(s) may be administered to the host using any convenient means capable of resulting in the desired reduction in a Tat deacetylase activity. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent (e.g., an agent that inhibits a SIRT1 Tat deacetylase activity) can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. An active agent (e.g., an agent that inhibits a SIRT1 Tat deacetylase activity) can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. An active agent (e.g., an agent that inhibits a SIRT1 Tat deacetylase activity) can be administered rectally via a suppository. The suppository can include vehicles such as cocoa butter, carbowaxes and polyethylene glycols, which melt at body temperature, yet are solidified at room temperature.

An active agent (e.g., an agent that inhibits a SIRT1 Tat deacetylase activity) may be formulated for vaginal administration. Pessaries, tampons, creams, gels, pastes, foams or sprays, may contain agents in addition to the bacteria, such carriers, known in the art to be appropriate.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent (e.g., an agent that inhibits a SIRT1 Tat deacetylase activity) calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

Other modes of administration will also find use with the subject invention. For instance, an active agent (e.g., an agent that inhibits a SIRT1 Tat deacetylase activity) can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An active agent (e.g., an agent that inhibits a SIRT1 Tat deacetylase activity) can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent (e.g., an agent that inhibits SIRT1 Tat deacetylase) will in some embodiments be formulated for vaginal delivery. A subject formulation for intravaginal administration is formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

A subject formulation comprising an active agent in some embodiments includes one or more of an excipient (e.g., sucrose, starch, mannitol, sorbitol, lactose, glucose, cellulose, talc, calcium phosphate or calcium carbonate), a binder (e.g., cellulose, methylcellulose; hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range of an active agent (e.g., an agent that inhibits a SIRT1 Tat deacetylase activity) is one which provides from about 1 µg to about 100 mg, e.g., from about 1 µg to about 10 µg, from about 10 µg to about 50 µg, from about 50 µg to about 100 µg, from about 100 µg to about 500 µg, from about 500 µg to about 1 mg, from about 1 mg to about 10 mg, from about 10 mg to about 20 mg, from about 20 mg to about 30 mg, from about 30 mg to about 40 mg, from about 40 mg to about 50 mg, from about 50 mg to about 60 mg, from about 60 mg to about 70 mg, from about 70 mg to about 80 mg, from about 80 mg to about 90 mg, or from about 90 mg to about 100 mg, of an active agent (e.g., an agent that inhibits a SIRT1 Tat deacetylase activity), administered in a single dose. Alternatively, a target dosage of an active agent (e.g., an agent that inhibits a SIRT1 Tat deacetylase activity) can be considered to be about in the range of about 0.1-1000 µM, about 0.5-500 µM, about 1-100 µM, or about 5-50 µM in a sample of host blood drawn within the first 24-48 hours after administration of the agent.

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition to reduce a symptom in an individual being treated.

Those of skill will readily appreciate that dose levels can vary as a function of the specific compound, the severity of the symptoms, the pharmacokinetic characteristics of the agent, and the susceptibility of the subject to side effects. Preferred dosages for a given compound are readily determinable by those of skill in the art by a variety of means.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

Routes of Administration

An active agent (e.g., an agent that inhibits a SIRT1 Tat deacetylase activity) is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, transdermal, subcutaneous, intradermal, topical application, intravenous, vaginal, nasal, and other parenteral routes of administration. Suitable routes of administration also include oral and rectal routes. Routes of administration may be combined, if desired, or adjusted depending upon the agent and/or the desired effect. The composition can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral, intranasal, and rectal (e.g., using a suppository) delivery. The agent can also be delivered to the subject intravaginally.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an allergic hypersensitivity. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Treatment Methods

The present invention provides treatment methods involving modulating a SIRT1 activity and/or a SIRT mRNA and/or polypeptide level. The present invention further provides methods of treating an immunodeficiency virus infection in an individual.

Treatment methods involving modulating a SIRT1 activity and/or a SIRT mRNA and/or polypeptide level in a cell in a mammalian subject are useful for treating any disorder that is amenable to treatment by modulating a SIRT1 activity and/or a SIRT mRNA and/or polypeptide level. "Modulating" includes "increasing" and "decreasing." In some embodiments, the disorder is an immunodeficiency virus infection.

In some embodiments of interest, the method involves administering to an individual in need thereof an amount of an agent that increases a SIRT1 activity and/or a SIRT mRNA and/or polypeptide level by at least about 10%, at least about 20%, at least about 30%, at least about 40%, at least about 50%, at least about 60%, at least about 70%, at least about 80%, at least about 90%, at least about 2-fold, at least about 5-fold, or at least about 10-fold, or more, compared to the SIRT1 level or activity in the absence of the agent.

In some embodiments of interest, the method involves administering to an individual in need thereof an amount of an agent that decreases a SIRT1 activity and/or a SIRT mRNA and/or polypeptide level by at least about 10%, at least about 20%, at least about 30%, at least about 40%, at least about 50%, at least about 60%, at least about 70%, at least about 80%, or at least about 90%, or more, compared to the SIRT1 level or activity in the absence of the agent.

Methods of Treating an Immunodeficiency Virus Infection

The present invention provides methods of treating an immunodeficiency virus infection in an individual. In one embodiment, the methods generally involve administering to an individual having an immunodeficiency virus infection an inhibitor of SIRT1 Tat deacetylase activity in an amount effective to inhibit SIRT1 Tat deacetylase activity in an immunodeficiency virus-infected cell in the individual, thereby treating the immunodeficiency virus infection. In another embodiment, the methods involve reducing SIRT1 expression or availability, e.g., using an agent that modulates SIRT1 transcription, translation, degradation, or localization. Such agents can be evaluated by screening cells that express SIRT1, e.g., from endogenous regulatory sequences and identifying agents that cause cells to have altered SIRT1 expression or availability. Exemplary agents include siRNA and gene therapy constructs.

In many embodiments, an agent that inhibits SIRT1 Tat deacetylase that is suitable for use in a subject treatment method inhibits SIRT1 Tat deacetylase activity by at least about 10%, at least about 15%, at least about 20%, at least about 25%, at least about 30%, at least about 40%, at least about 50%, at least about 60%, at least about 70%, at least about 80%, or at least about 90%, or more, compared to the SIRT1 Tat deacetylase activity in the absence of the compound.

In many embodiments, an agent that inhibits SIRT1 Tat deacetylase that is suitable for use in a subject treatment method is a selective inhibitor of SIRT1 Tat deacetylase. An agent that is a selective inhibitor of SIRT1 Tat deacetylase activity is an agent that does not substantially inhibit other enzymes, including, e.g., SIRT2 or SIRT3, e.g., at the $IC_{50}$ for SIRT1, the agent does not result in more than about 5%, more than about 10%, or more than about 25% inhibition of SIRT2 or SIRT3 enzymatic activity.

The term "selective inhibitor of SIRT1 Tat deacetylase" is used herein to mean compound which selectively inhibits SIRT1 Tat deacetylase activity in preference to SIRT2 (or any other enzyme) and particularly a compound for which the ratio of the $IC_{50}$ concentration (concentration inhibiting 50% of activity) for SIRT1 Tat deacetylase to the $IC_{50}$ concentration for SIRT2 is greater than 1. Such ratio is readily determined by assaying for SIRT1 Tat deacetylase activity and assaying for SIRT2 activity and from the resulting data obtaining a ratio of $IC_{50}$s.

Agents that inhibit SIRT1 Tat deacetylase activity and that are suitable for use in a subject treatment method inhibits SIRT1 Tat deacetylase activity with an $IC_{50}$ of less than about 50 µM, e.g., a suitable agent inhibits SIRT1 Tat deacetylase activity with an $IC_{50}$ of less than about 40 µM, less than about 25 µM, less than about 10 µM, less than about 1 µM, less than about 100 nM, less than about 80 nM, less than about 60 nM, less than about 50 nM, less than about 25 nM, less than about 10 nM, or less than about 1 nM, or less.

In some embodiments, a therapeutically effective amount of an agent that inhibits SIRT1 Tat deacetylase activity is an amount that reduces immunodeficiency virus load in the individual and/or reduces immunodeficiency virus replication in an immunodeficiency virus-infected cell in the individual by at least about 10%, at least about 20%, at least about 30%, at least about 40%, at least about 50%, at least about 60%, at least about 70%, at least about 80%, at least about 90%, or at least about 95% or more, compared to the immunodeficiency virus load or immunodeficiency virus replication in an immunodeficiency virus-infected cell of the individual not treated with the agent.

In some embodiments, a therapeutically effective amount of an agent that SIRT1 Tat deacetylase activity is an amount that reduces the pool of actively replicating virus in a plasma sample collected from the subject to less than about 5000 RNA molecules/ml, less than about 4000 RNA molecules/ml, less than about 3000 RNA molecules/ml, less than about 2000 RNA molecules/ml, or less than about 1000 RNA molecules/ml. In some embodiments, an effective amount of an agent that SIRT1 Tat deacetylase activity is an amount that reduces the pool of actively replicating virus in a plasma sample collected from the subject to an undetectable amount. By "undetectable amount" in the plasma is intended the amount of actively replicating immunodeficiency virus is less than about 500 RNA molecules/ml, less than about 400 RNA molecules/ml, less than about 300 RNA molecules/ml, less than about 200 RNA molecules/ml, less than about 100 RNA molecules/ml, or less than about 50 RNA molecules/ml.

In some embodiments, a therapeutically effective amount of an agent that inhibits SIRT1 Tat deacetylase activity is an amount that increases $CD4^+$ T cell numbers in an immunodeficiency virus-infected cell in the individual by at least about 10%, at least about 20%, at least about 30%, at least about 40%, at least about 50%, at least about 60%, at least about 70%, at least about 80%, at least about 90%, at least about 100%, at least about 2.5-fold, at least about 3-fold, at least about 3.5-fold, at least about 4-fold, at least about 5-fold, or at least about 10-fold, or more, compared to the $CD4^+$ T cell count of the individual not treated with the agent. In some embodiments, a therapeutically effective amount of an agent that inhibits SIRT1 Tat deacetylase activity is an amount that restores the $CD4^+$ T cell count to within a normal range. In human blood, the number of $CD4^+$-T cells which is considered to be in a normal range is from about 600 to about 1500 $CD4^+$-T cells/mm$^3$ blood.

Any method known to those skilled in the art may be utilized to measure viral load in the plasma. As one non-limiting example, plasma viral load can be determined using a branched chain DNA assay (bDNA), which has a lower limit of detection (LLD) of 50 HIV RNA molecules/ml (see Jacobson et al. (1996) Proc. Natl. Acad. Sci. USA 93:10405-10410; herein incorporated by reference). When an undetectable amount of replicating virus is present in a plasma sample obtained from an HIV-infected subject, plasma viral RNA is said to be "undetectable" in the subject.

Treating an immunodeficiency virus infection, includes, but is not limited to, preventing immunodeficiency virus infection, reducing the probability of immunodeficiency virus infection, reducing the spread of immunodeficiency virus from an infected cell to a susceptible cell, reducing viral load in an immunodeficiency virus-infected individual, reducing an amount of virally-encoded polypeptide(s) in an immunodeficiency virus-infected individual, and increasing CD4 T cell count in an immunodeficiency virus-infected individual.

The amount of subject agent which is administered will vary with the nature of the drug. As one non-limiting example, a subject agent can be administered in the range of about 0.2 to 20 mg/kg/day. The determination of how large a dosage to be used may be determined using the small animal model and relating the dosage based on pharmacokinetics, e.g. with equations predictive of interspecies scaling. Usually, the lowest effective dose will be used.

Any of a variety of methods can be used to determine whether a treatment method is effective. For example, methods of determining whether the methods of the invention are effective in reducing immunodeficiency virus entry into a cell, and/or treating an immunodeficiency virus infection, are any known test for indicia of immunodeficiency virus infection, including, but not limited to, measuring viral load, e.g., by measuring the amount of immunodeficiency virus in a biological sample, e.g., using a polymerase chain reaction (PCR) with primers specific for an immunodeficiency virus polynucleotide sequence and/or using a hybridization probe(s) specific for an immunodeficiency virus; detecting and/or measuring a polypeptide encoded by immunodeficiency virus, e.g., p24, gp120, reverse transcriptase, using, e.g., an immunological assay with an antibody specific for the polypeptide; and measuring CD4 cell count in the individual. Methods of assaying an immunodeficiency virus infection (or any indicia associated with an immunodeficiency virus infection) are known in the art, and have been described in numerous publications such as *HIV Protocols* (*Methods in Molecular Medicine*, 17) N. L. Michael and J. H. Kim, eds. (1999) Humana Press; and U.S. Pat. No. 6,649,749.

Combination Therapies

An active agent (an agent that selectively inhibits SIRT1 activity) is in some embodiments administered to an individual in combination (e.g., in the same formulation or in separate formulations) with at least a second therapeutic agent ("combination therapy"). An active agent (an agent that selectively inhibits SIRT1 activity) is in some embodiments administered in admixture with a second therapeutic agent or can be administered in a separate formulation. When administered in separate formulations, an active agent and at least a second therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more. Effective amounts of a therapeutic agent are as described above.

Therapeutic agents that can be administered in combination with a SIRT1 Tat deacetylase inhibitor include agents that inhibits one or more immunodeficiency virus functions, which functions include, but are not limited to, viral replication; viral protease activity; viral reverse transcriptase activity; viral entry into a cell; viral integrase activity; activity of one or more of Rev, Tat, Nef, Vpr, Vpu, and Vif; and the like.

Therapeutic agents that can be administered in combination therapy with a subject SIRT1 Tat deacetylase inhibitor include, but are not limited to, anti-inflammatory agents, anti-viral agents, anti-fungal agents, anti-mycobacterial agents, antibiotics, amoebicidal agents, trichomonocidal agents, analgesics, anti-neoplastic agents, anti-hypertensives, anti-microbial agents, or combinations of the foregoing.

Therapeutic agents that can be administered in combination therapy with a subject SIRT1 Tat deacetylase inhibitor include side effect management agents, e.g., agents that reduce one or more side effects of an anti-immunodeficiency virus drug. Side effects include, but are not limited to, anemia, leukopenia, anorexia, arthralgia, chills, fever, diarrhea, constipation, headache, myalgia, neuropathy, rash, vomiting, and the like. Suitable side effect management agents include, but are not limited to, anti-emetics, anti-inflammatory agents, and agents that increase production of one or more blood cell types.

In some embodiments, a subject combination therapy involves administering an effective amount of an agent that inhibits SIRT1 Tat deacetylase activity, and an effective amount of one or more of the following; a beta-lactam antibiotic, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), zidovudine/lamivudine (Combivir), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AZDU, delavirdine (Rescriptor™), lopinavir/ritonavir (Kaletra), MIV-150, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

In some embodiments, a subject combination therapy involves administering an effective amount of an agent that inhibits SIRT1 Tat deacetylase activity; and an effective amount of a non-nucleoside reverse transcriptase inhibitor. As used herein, the term "non-nucleoside reverse transcriptase HIV inhibitor" (NNRTI) includes, but is not limited to, delavirdine, (Pharmacia and Upjohn U90152S), efavirenz (DuPont Pharmaceuticals), nevirapine (Boehringer Ingelheim), RO 18,893 (Roche), trovirdine (Lilly), MKC-442 (Triangle), HBY 097 (Hoechst), ACT (Korean Research Institute), UC-781, (Rega Institute), UC-782, (Rega Institute), RD4-2025 (Tosoh Co. Ltd.), MEN 10970 (Menarini Farmacuetici), TIBO derivatives, BI-RG-587, L 697,661, LY 73497, and loviride (Jannsen). additional examples include (−)-6-chloro-4-cyclopropylethynyl-4-trifluoromethyl-3,4-dihydro-2 (1H)-quinazolinone), "Compound A"; (+)-4-Cyclopropylethynyl-5,6-difluoro-4-trifluoromethyl-3,4-dihydro-2 (1H)-quinazolinone), "Compound B"; (+)-4-cyclopropylethenyl-5,6-difluro-4-trifluoromethyl-3,4-dihydro-2(1H)-quinazolinone, "Compound C"; and (−)-6-chloro-4-E-cyclopropylethenyl-4-trifluoromethyl-3,4-dihydro-2(1H)-quinazolinone, "Compound D" (DuPont Pharmaceuticals), NNRTIs disclosed in U.S. Pat. No. 6,124,302. Another suitable NNRTI is MIV-150 (Medivir).

In some embodiments, a subject combination therapy involves administering an effective amount of an agent that inhibits SIRT1 Tat deacetylase activity; and an effective amount of a nucleoside analog immunodeficiency virus inhibitor. Nucleoside analogs are exemplified by didanosine (2',3'-dideoxyinosine or [ddI], available as Videx™ from Bristol Myers-Squibb, Wallingford, Conn.); zidovudine (3'-azido-2',3'-dideoxythymidine or azidothymidine [AZT], available from Glaxo-Wellcome Co., Research Triangle Park, N.C.); zalcitabine (2',3'-dideoxycytidine [ddC], available as Hivid™ from Hoffman-La Roche, Basel, Switzerland); lamivudine 2'-deoxy-3'-thiacytidine [3TC] (Epivir™, available from Glaxo-Wellcome Co.); stavudine (2',3'-didehydro-2',3'-dideoxythimidine [D4T] available as Zerit™) from Bristol Myers-Squibb); and the combination drug zidovudine plus lamivudine (Combivir™, available from Glaxo Wellcome). These particular drugs belong to the class of compounds known as 2',3'-dideoxynucleoside analogs, which, with some exceptions such as 2',3'-dideoxyuridine [DDU], are known to inhibit HIV replication, but have not been reported to clear any individual of the virus. Other nucleoside reverse transcriptase inhibitors include abacavir (1592U89, Ziagen™, available from Glaxo-Wellcome Co.).

In some embodiments, a subject combination therapy involves administering an effective amount of an agent that inhibits SIRT1 Tat deacetylase activity; and an effective amount of a protease inhibitor-type immunodeficiency virus inhibitor. Examples of protease inhibitors useful in the present invention include, but are not limited to, Indinavir sulfate (available as Crixivan™ capsules from Merck & Co., Inc., West Point, Pa.), saquinavir (Invirase™ and Fortovase™, available from Hoffmnan-La Roche), ritonavir (Norvir™, available from Abbott Laboratories, Abbott Park, Ill.); ABT-378 (new name: lopinavir, available from Abbott Laboratories); Amprenavir (Agenerase™, available from Glaxo Wellcome, Inc.); and Nelfinavir (Viracept™), and GW141 (available from Glaxo Wellcome/Vertex).

In some embodiments, an agent that inhibits SIRT1 Tat deacetylase is administered in combination therapy with two or more anti-HIV agents. For example, an agent that inhibits SIRT1 Tat deacetylase can be administered in combination therapy with one, two, or three nucleoside reverse transcriptase inhibitors (e.g., Combivir, Epivir, Hivid, Retrovir, Videx, Zerit, Ziagen, etc.). An agent that inhibits SIRT1 Tat deacetylase can be administered in combination therapy with one or two non-nucleoside reverse transcriptase inhibitors (e.g., Rescriptor, Sustiva, Viramune, MIV-150, etc.). An agent that inhibits SIRT1 Tat deacetylase can be administered in combination therapy with one or two protease inhibitors (e.g., Agenerase, Crixivan, Fortovase, Invirase, Kaletra, Norvir, Viracept, etc.). An agent that inhibits SIRT1 Tat deacetylase can be administered in combination therapy with a protease inhibitor and a nucleoside reverse transcriptase inhibitor. An agent that inhibits SIRT1 Tat deacetylase can be administered in combination therapy with a protease inhibitor, a nucleoside reverse transcriptase inhibitor, and a non-nucleoside reverse transcriptase inhibitor. An agent that inhibits SIRT1 Tat deacetylase can be administered in combination therapy with a protease inhibitor and a non-nucleoside reverse transcriptase inhibitor. Other combinations of an agent that inhibits SIRT1 Tat deacetylase with one or more of a protease inhibitor, a nucleoside reverse transcriptase inhibitor, and a non-nucleoside reverse transcriptase inhibitor are contemplated.

Guidance as to dosages for any given antiretroviral agent is available in the art and includes administering commercially available agents at their recommended dosages. See, for example, Medical Letter 42(Jan. 10, 2000):1-6, herein incorporated by reference. Thus, for example, IDV can be administered at a dosage of about 800 mg, three times a day; D4T can be administered at a dosage of about 30-40 mg, twice a day; and Nelfinavir can be administered at a dosage of about 1250 mg, twice a day, or 750 mg three times a day. These agents are generally administered in oral formulations, though any suitable means of administration known in the art may be utilized for their delivery.

For example, an agent that inhibits SIRT1 Tat deacetylase is administered in combination therapy with one or more nucleoside reverse transcriptase inhibitors (RTI's; where nucleoside reverse transcriptase inhibitors include AZT, ddI, 3TC, ddC, d4T, and abacavir); and/or one or more protease inhibitors (where protease inhibitors include indinavir, saquinavir, ritonavir, nelfinavir, amprevanir, and lopinavir); and/or one or more non-nucleoside reverse transcriptase inhibitors (where non-nucleoside reverse transcriptase inhibitors include nevirapine, delavirdine, emiravine, and efavirenz); and/or a fusion inhibitor (e.g., T20, T-1249); and/or a CCR5 blocker (e.g., SCH-C, SCH-D).

An agent that inhibits SIRT1 Tat deacetylase can be administered to an individual in combination with any highly active antiretroviral therapy (HAART) or Structured Treatment Interruptions (STI) regimens currently in use.

Kits, Containers, Devices, Delivery Systems

Kits with unit doses of an active agent (an agent that selectively inhibits SIRT1 Tat deacetylase activity), e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating an HIV infection. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

The present invention provides a delivery system comprising an active agent (an agent that selectively inhibits SIRT1 Tat deacetylase activity). In some embodiments, the delivery system is a delivery system that provides for injection of a formulation comprising an active agent (an agent that selectively inhibits SIRT1 Tat deacetylase activity) subcutaneously, intravenously, or intramuscularly. In other embodiments, the delivery system is a vaginal delivery system.

In some embodiments, an active agent is packaged for oral administration. The present invention provides a packaging unit comprising daily dosage units of an active agent. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a subject delivery system comprises an injection device. Exemplary, non-limiting drug delivery devices include injections devices, such as pen injectors, and needle/syringe devices. In some embodiments, the invention provides an injection delivery device that is pre-loaded with a formulation comprising an effective amount of an active agent (an agent that selectively inhibits SIRT1 Tat deacetylase activity). For example, a subject delivery device comprises an injection device pre-loaded with a single dose of an active agent (an agent that selectively inhibits SIRT1 Tat deacetylase activity). A subject injection device can be re-usable or disposable.

Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; and the like. The medication delivery pen can be disposable, or reusable and refillable.

The present invention provides a vaginal delivery system for vaginal delivery of an active agent (an agent that selectively inhibits SIRT1 Tat deacetylase activity) to the vagina of an individual. The delivery system comprises a device for insertion into the vagina. In some embodiments, the delivery system comprises an applicator for delivery of a formulation into the vagina; and a container that contains a formulation comprising an active agent (an agent that selectively inhibits SIRT1 Tat deacetylase activity). In these embodiments, the container (e.g., a tube) is adapted for delivering a formulation into the applicator. In other embodiments, the delivery system comprises a device that is inserted into the vagina, which device includes an active agent (an agent that selectively inhibits SIRT1 Tat deacetylase activity). For example, the device is coated with, impregnated with, or otherwise contains a formulation comprising the active agent.

In some embodiments, the vaginal delivery system is a tampon or tampon-like device that comprises a subject formulation. Drug delivery tampons are known in the art, and any-such tampon can be used in conjunction with a subject drug delivery system. Drug delivery tampons are described in, e.g., U.S. Pat. No. 6,086,909. If a tampon or tampon-like device is used, there are numerous methods by which an active agent (an agent that selectively inhibits SIRT1 Tat deacetylase activity) can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal ring. Vaginal rings usually consist of an inert elastomer ring coated by another layer of elastomer containing an active agent (an agent that selectively inhibits SIRT1 Tat deacetylase activity) to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal delivery system is a vaginal sponge. The active agent is incorporated into a silicone matrix which is coated onto a cylindrical drug-free polyurethane vaginal sponge, as described in the literature.

Pessaries, tablets and suppositories are other examples of drug delivery systems which can be used in the present invention. These systems have been described extensively in the literature.

Bioadhesive microparticles constitute still another drug delivery system suitable for use in the present invention. This system is a multi-phase liquid or semi-solid preparation which does not seep from the vagina as do many suppository formulations. The substances cling to the wall of the vagina and release the drug an active agent (an agent that selectively inhibits SIRT1 Tat deacetylase activity) over a period of time. Many of these systems were designed for nasal use but can be used in the vagina as well (e.g. U.S. Pat. No. 4,756,907). The system may comprise microspheres with an active agent; and a surfactant for enhancing uptake of the drug. The microparticles have a diameter of 10-100 pm and can be prepared from starch, gelatin, albumin, collagen, or dextran.

Another system is a container comprising a subject formulation (e.g., a tube) that is adapted for use with an applicator. The active agent (an agent that selectively inhibits SIRT1 Tat deacetylase activity) is incorporated into creams, lotions, foams, paste, ointments, and gels which can be applied to the vagina using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

Subjects Suitable for Treatment

The methods of the present invention are suitable for treating individuals suffering from any disorder that is amenable to treatment by modulating a SIRT1 activity level and/or a SIRT1 mRNA and/or polypeptide level.

The methods of the present invention are suitable for treating individuals who have an immunodeficiency virus infection; who are at risk of contracting an immunodeficiency virus infection; and who were treated for an immunodeficiency virus infection, but who relapsed. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals; intravenous drug users; individuals who may have been exposed to HIV-infected blood, blood products, or other HIV-contaminated body fluids; and babies who are being nursed by HIV-infected mothers. Individuals suitable for treatment include individuals infected with, or at risk of becoming infected with, HIV-1 and/or HIV-2 and/or HIV-3, or any variant thereof.

Individuals suitable for treatment with the methods of the invention also include individuals who have an immunodeficiency virus infection that is refractory to treatment with other anti-viral therapies.

In some cases, an HIV infected individual is CD4$^+$ deficient, or CD4$^+$ low. The terms "CD4$^+$-deficient" and "CD4$^+$-low" are used interchangeably herein, and, as used herein, refer to a state of an individual in whom the number of CD4$^+$ T lymphocytes is reduced compared to an individual with a healthy, intact immune system. CD4$^+$ deficiency includes a state in which the number of functional CD4$^+$ T lymphocytes is less than about 600 CD4$^+$T cells/mm$^3$ blood; a state in which the number of functional CD4$^+$T cells is reduced compared to a healthy, normal state for a given individual; and a state in which functional CD4$^+$ T cells are completely absent. As used herein, a "CD4$^+$-deficient individual" is one who has a reduced number of functional CD4$^+$-T cells, regardless of the reason, when compared to an individual having a normal, intact immune system. In general, the number of functional CD4$^+$-T cells that is within a normal range is known for various mammalian species.

Also suitable for treatment with a subject method are individuals who were treated for an immunodeficiency virus infection, but who relapsed, e.g., whose CD4$^+$ T cell count was increasing in response to anti-viral therapy for HIV, but whose CD4$^+$ T cell counts subsequently began to fall ("relapse" patients).

The methods of the present invention are suitable for treating individuals who failed treatment with previous anti-viral therapy for the treatment of an HIV infection. ("treatment failure patients"). Such treatment failure patients include individuals who have undergone previous HAART or STI treatment regimens.

Also suitable are individuals who were previously treated with anti-retroviral therapy for the treatment of an HIV infection, and in whom drug-resistant HIV has emerged.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); hr, hour(s); the term "α-FLAG" refers to "anti-FLAG antibody"; and the like.

Example 1

SIRT1 is an HIV Tat Deacetylase

The data presented below demonstrate that SIRT1 is a Tat deacetylase; and that inhibitors of SIRT1 inhibit Tat activity.

Materials and Methods

Cells and Plasmids

HeLa, HEK 293 and Jurkat cells (obtained from the American Type Culture Collection) and wildtype or Sir2α knockout mouse embryonic fibroblasts (McBurney et al. (2003) Mol Cell Biol 23: 38-54) were maintained under standard cell culture conditions. The HIV LTR luciferase plasmid (Emiliani et al. (1998) J Virol 72: 1666-1670), the RSV LTR luciferase construct (Kaehlcke et al. (2003) Mol Cell 12: 167-176) the 5×UAS luciferase construct (Puigserver et al. (1999) Science 286: 1368-1371), the LTR$_{\Delta NF-kB}$-luciferase, the full-length (101 amino acid) CMV-Tat-FLAG and CMV-Tat-T7 expression vectors (Ott et al. (1999) Curr Biol 9: 1489-1492), the full-length (101 amino acid) RSV-Tat expression vector (Ott et al. (1997) Science 275: 1481-1485), the full-length CyclinT1 expression vector (Wei et al. (1998) Cell 92: 451-462), the Gal4/VP16 expression vector (Dorr et al. (2002) EMBO J. 21: 2715-2723), the human SIRT1-7 expression vectors with a C-terminal FLAG tag (Onyango et al. (2002) Proc Natl Acad Sci USA 99: 13653-13658) as well as wildtype and mutant human SIRT1 and SIRT1H363Y containing a C-terminal MYC tag (Langley et al. (2002) EMBO J. 21: 2383-2396) were previously described.

The SIRT1 cDNA was subcloned to generate a C-terminal HA-tagged fusion in a derivative pcDNA 3.1 (+) backbone (HA vector) by standard PCR-based strategies. The mutant CMV-Tat-FLAG expression vector (TatK50R) was generated by site-directed mutagenesis with the following primers 5' cctatggcaggaggaagcggagacagcg 3' (forward; SEQ ID NO:3) and 5' cgctgtctccgcttcctcctgccatagg 3' (reverse; SEQ ID NO:4). The mutant HIV LTR luciferase constructs (nt 1-791) were generated by site-directed mutagenesis with the following primers: TAR Δbulge (T223→A) 5' ggttagaccagaactgagcctgggagc 3' (forward; SEQ ID NO:5) and 5'gctcccaggctcagttctggtctaacc 3' (reverse; SEQ ID NO:6). The TAR Δloop mutation (C230→A, T231→G and G234→T) was generated with 5' ggttagaccagatctgagcagggtagctctctggctaactaggg 3' (forward; SEQ ID NO:7) and 5'ccctagttagccagagagctaccctgctcagatctggtctaacc 3' (reverse; SEQ ID NO:8) primers.

The CMV-luciferase construct was generated by cloning the luciferase gene as a HindIII/BamHI fragment obtained from pGL2 Basic (Promega) into pcDNA3.1 (Invitrogen, Carlsbad, Calif.). The CMV-GFP expression plasmid is commercially available (Clontech, Palo Alto, Calif.).

Synthesis of Tat and HR73

Synthesis of 72-amino acid Tat proteins was as described. Kaehlcke et al. (2003), supra; and Dorr et al. (2002), supra. HR73 was synthesized starting from Phenylmeldrum's acid and 6-bromo-1-dimethylaminomethyl-2-naphthol according to Jacobs et al. ((1982) J Org Chem 47: 3769-3772). Identity and purity were assured by mass spectroscopy, infrared and NMR spectroscopy as well as by elemental analysis.

In Vitro Tat Deacetylation Assay

Human SIRT1-7 FLAG-tagged plasmids were transfected in 293 cells with lipofectamine reagent (Invitrogen). Cells were lysed 24 hours after transfection with lysis buffer (50 mM Tris-Hcl, pH 7.5, 0.5 mM EDTA, 0.5% NP40, 150 mM NaCl) in the presence of protease inhibitors (Roche Molecular Biochemicals, Indianapolis, Ind.). Equal amounts of total proteins were immunoprecipitated with α-FLAG (anti-FLAG antibody) coupled to M2 agarose beads (Sigma, St Louis, Mo.), for 2 hours at 4° C. Immunoprecipitated material was washed twice with immunoprecipitation (IP) buffer and one time with SIRT deacetylation buffer (50 mM Tris-HCl pH 9, 4 mM $MgCl_2$, 0.2 mM DTT). The beads were resuspended in 100 µl SIRT deacetylation buffer containing 1 µg synthetic Tat (72 amino acids) carrying an N-terminal biotin label and an acetyl group at position 50. Kaehlcke et al. (2003), supra. Reactions containing TSA (400 nM, WACO Bioproducts, Richmond, Va.) or nicotinamide (5 mM, Sigma) were preincubated for 10 min at room temperature. After addition of $NAD^+$ (1 mM) reactions were incubated for 2 hours at room temperature with constant agitation. Reactions were stopped by the addition of SDS loading buffer, boiled, and after brief centrifugation, analyzed by western blotting with rabbit α-AcTat antibodies (Kaehlcke et al. (2003), supra) or horseradish peroxidase-conjugated streptavidin (Jackson Immunoresearch Laboratories, West Grove, Pa.). SIRT1-7 proteins were detected with polyclonal α-FLAG antibodies (Sigma).

The histone deacetylation assay with recombinant SIRT1 (1-1.3 U/reaction; Biomol, Plymouth Meeting, Pa.) was performed as described previously for SIRT2 (North et al. (2003) Mol Cell 11: 437-444) in 100 µl SIRT deacetylase buffer containing $NAD^+$ (Sigma) and enzymatically [$^3$H] acetylated histone H3 peptide (amino acids 1-24). Borra et al. (2002) J Biol Chem 277: 12632-12641. Splitomicin (a gift from Julian Simon, Fred Hutchinson Cancer Research Center, Seattle, Wash.) and HR73 in dimethylsulfoxide (DMSO) were added to the reactions at the indicated concentrations with all components of the reactions in the absence of $NAD^+$ for 10 min at room temperature prior to the initiation of the reaction by addition of $NAD^+$ (1 mM).

Co-Immunoprecipitation Experiments 293 cells were co-transfected in duplicate with expression vectors for CMV-Tat/FLAG, CMV-Tat/T7 or CMV-TatK50R/FLAG and the SIRT1-HA or SIRT1-, 2- and 6-FLAG expression vectors or the respective empty vector controls using lipofectamine reagent (Invitrogen). Cells were lysed after 24 hours in 250 mM NaCl, 0.1% NP40, 20 mM $NaH_2PO_4$, pH 7.5, 5 mM EDTA, 30 mM sodium pyrophosphate, 10 mM NaF, and protease inhibitors (Roche Molecular Biochemicals). Duplicates were pooled, and 1 mg of lysate was immunoprecipitated either with monoclonal α-HA (anti-hemagglutinin antibody) (Roche Molecular Biochemicals) together with protein G-Sepharose (Amersham Biosciences, Piscataway, N.J.) with α-FLAG M2 agarose (Sigma) or α-T7-agarose (anti-T7 antibody coupled to agarose beads) (Amersham Biosciences) for 2 hours at 4° C. Beads were washed three times in lysis buffer, boiled in sodium dodecyl sulfate (SDS) loading buffer, and analyzed by western blotting with polyclonal α-FLAG (Sigma), monoclonal α-HA (Roche) or monoclonal α-T7 (Novagen, Madison, Wis.) antibodies. For the immunoprecipitation of Tat with endogenous SIRT1, 293 cells were transfected only with CMV-Tat/FLAG or the CMV-empty vector using lipofectamine reagents. Cell lysates were immunoprecipitated with rabbit α-SIRT1 antibodies (generated against amino acid 506-747) together with Protein G-Sepharose (Amersham Biosciences). Immunoprecipitated material was analyzed by western blotting with the M2 α-FLAG antibody (Sigma) or rabbit α-SIRT1 antibodies.

For in vitro interactions, 10 units of recombinant SIRT1 (Biomol) were incubated with biotinylated synthetic Tat or acetylated Tat proteins (0 µg, 0.25 µg, 1 µf, and 4 µg) together with streptavidin-Sepharose high performance (Amersham Biosciences) in lysis buffer in the presence of 5 mM nicotinamide (Sigma) 3 hours at 4° C. Pelleted beads were washed three times in lysis buffer, resuspended in SDS loading buffer and analyzed by western blotting with polyclonal α-SIRT1 antibodies, rabbit α-AcARM (10 g/ml) or horse radish peroxidase (HRP)-conjugated streptavidin (Jackson Immunoresearch Laboratories).

RNAi and Transfection Experiments

Double-stranded siRNAs directed against nt 408-428 in the SIRT1 mRNA or control siRNAs against GL3 luciferase (both Dharmacon Research, Lafayette, Colo.) were transfected into HeLa cells plated in six-well plates with Oligofectamine™ transfection reagent according to the manufacturer's guidelines (Invitrogen). The mutant SIRT1 siRNA was identical to SIRT1 siRNA except for a 2-nucleotide mismatch between the target mRNA for SIRT1 and the antisense strand of siRNA at nt 418 and 419. After 48 hours, cells were re-transfected with the HIV LTR luciferase construct (200 ng) together with increasing amounts of CMV-Tat expression vectors (0 ng, 50 ng, 100 ng, 200 ng, 400 ng, and 800 ng in GL3/SIRT1 siRNA experiments; 0 ng, 2 ng, 20 ng, and 200 ng in SIRT1/mutant SIRT1 siRNA experiments) and corresponding amounts of empty pcDNA3.1 vector (Invitrogen). In the control experiment, CMV-Tat was replaced by the CMV-luciferase construct, and HIV LTR luciferase was replaced by an HIV LTR promoter construct driving the expression of chloramphenicol acetyl transferase (HIV LTR CAT; Emiliani et al. (1996) Proc Natl Acad Sci USA 93: 6377-6381). Cells were harvested 24 hours later and either processed for luciferase assays (Promega) or western blotting of total cell extracts with polyclonal α-SIRT1 or α-actin (MP Biochemicals, Aurora, Ohio) antibodies.

In co-transfection experiments, human CMV-SIRT1 or CMV-SIRT1H363Y (600 ng) was co-transfected into HeLa cells plated in six-well plates with the HIV LTR luciferase reporter (200 ng) or the $LTR_{\Delta NF-kB}$-luciferase reporter (200 ng) and increasing amounts of RSV-Tat (0 ng, 2 ng, 20 ng, and 200 ng) using the lipofectamine reagents (Invitrogen). In the control experiment, RSV-Tat was replaced by RSV luciferase (200 ng), and the HIV LTR luciferase construct was replaced by the HIV LTR CAT reporter. In transfections with HR73, HeLa cells were co-transfected with the HIV LTR-luciferase reporter (200 ng) and RSV-Tat expression vectors (0 ng, 20 ng, and 200 ng) or the empty vector using lipofectamine reagent. The RSV-luciferase construct was used as described above. After 4 hours incubation with the DNA/lipofectamine mix, the culture media was changed and supplemented with indicated concentrations of HR73 in DMSO or DMSO alone. Cells were harvested 8 hr later and processed for luciferase assays.

Microinjection Experiments

Subconfluent MEFs (70%) were grown on Cellocate coverslips (Eppendorf, Westbury, N.Y.), and nuclear microinjections were performed at room temperature with an automated injection system (Eppendorf Micromanipulator 5171 together with Eppendorf Transjector 5246). Samples were prepared as a 20 µl injection mix containing the HIV LTR luciferase reporter or 5×UAS luciferase (each 100 ng/µl), RSV-Tat (10 ng/µl) or Gal4-VP16 (50 ng/µl), CMV-CyclinT1 (100 ng/µl), CMV-SIRT1 (100 or 300 ng/µl) together with CMV-GFP (50 ng/µl) in sterile water. Six hours after microinjection, cells were examined under a Nikon Eclipse TE300 inverted fluorescent microscope to determine the number of GFP-positive cells, washed in cold phosphate buffer, and stored at −70° C. for luciferase assays (Promega). In HeLa cells, synthetic Tat or AcTat proteins (each 30 or 100 ng/µl) were co-injected with the wildtype or mutant HIV LTR luciferase reporters (each 100 ng/µl) together with CMV-GFP (50 ng/µl) and harvested four hours after injection. Cells were treated immediately after injection with 5,6-dichlorobenzimidazole riboside (DRB; 10 or 50 µM; Sigma), TSA (400 nM), or nicotinamide (5 mM). Microinjections in siRNA-treated cells were performed 48 hours after siRNA transfection.

Viral Infection Experiments

The HIV molecular clone (HIV-R7/E−/GFP) containing the GFP open reading frame in place of the nef gene and a frameshift mutation in the env gene as well as the method to generate pseudotyped viral particles with VSV-G was previously described. Jordan et al. (2003) Embo J 22: 1868-1877. The number of infective particles per ml was established by infecting $3 \times 10^5$ Jurkat cells with different amounts of viral suspension. The titer of the viral stock was measured by flow cytometry analysis of GFP expression 48 hours after infection. The pHR'-EF-1α/GFP construct is a minimal nonreplicative HIV-1 genome containing a heterologous promoter (EF-1α) driving GFP expression. Naldini et al. (1996) Science 272: 263-267. Viral particles were produced by co-transfection of the VSV-G-encoding pMD.G and the HIV-based packaging vector pCMVΔR8.91 as described. Zufferey et al. (1997) Nat Biotechnol 15: 871-875. All vectors for the production of HIV-based lentiviral vectors were provided by D. Trono, University of Geneva, Switzerland. Jurkat T cells were incubated overnight with HIV-R7/E−/GFP or pHR'-EF-1α/GFP viral particles at a theoretical multiplicity of infection (m.o.i.) of 0.5 in 24-well plates. Cells were repeatedly washed and resuspended in fresh media containing HR73 (1 µM) or DMSO alone. Viral infection was monitored 36 hours later by flow cytometry analysis using a Calibur FACScan (Becton Dickinson).

Results

To test the ability of SIRT1-7 to deacetylate Tat in vitro, 293 cells were transfected with expression vectors for human SIRT1-7 and the FLAG-tagged proteins were immunoprecipitated, as depicted schematically in FIG. 1.

FIG. 1. In vitro Tat deacetylation by human SIRT proteins. Scheme of Tat deacetylation assay with immunoprecipitated SIRT1-7 proteins.

Figure 2A:
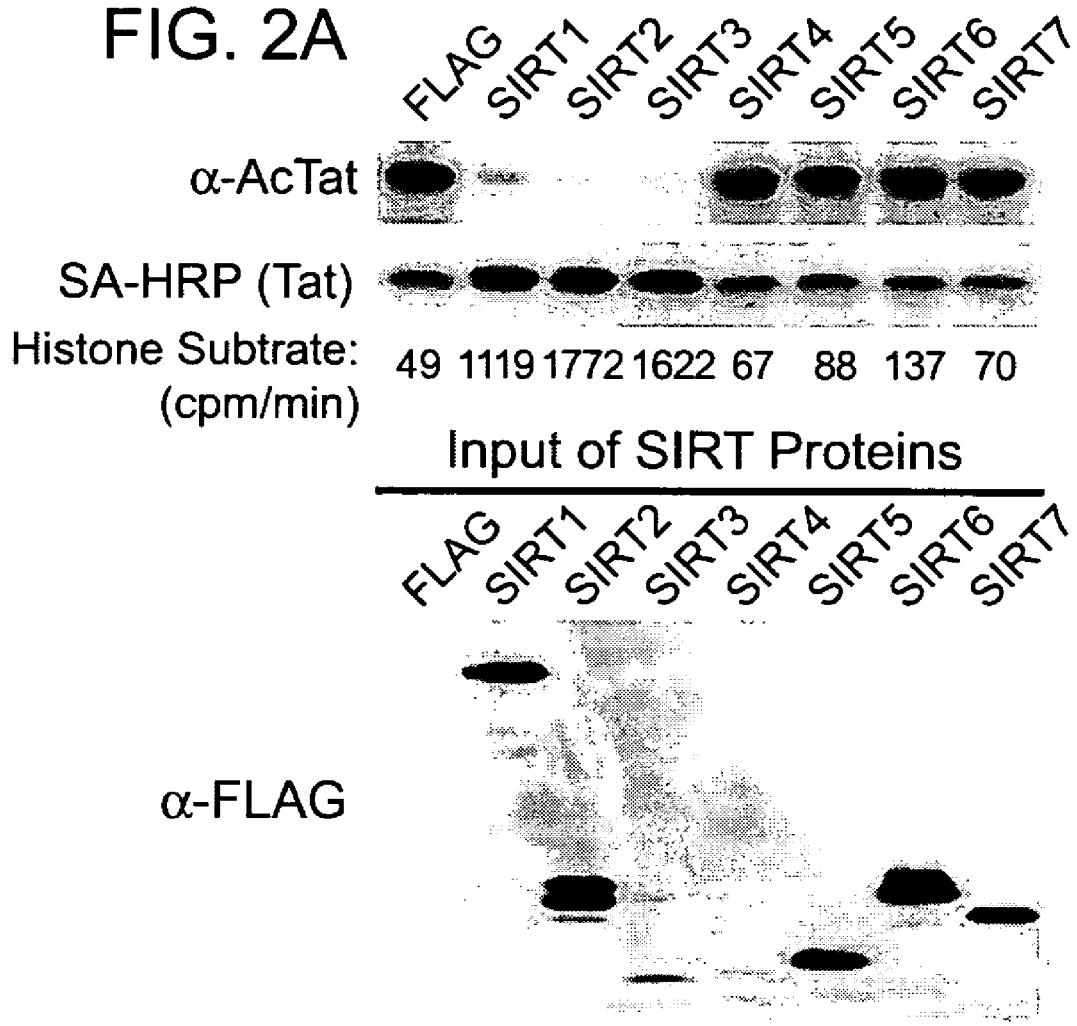
FIGS. 2A and 2B depict in vitro Tat deacetylation by human SIRT proteins.

The immunoprecipitated material was incubated with a full-length synthetic Tat protein carrying an acetylated lysine at position 50 (AcTat). The extent of Tat deacetylation was determined by western blotting with antibodies specific for the acetylated ARM in Tat. Kaehlcke et al. (2003), supra. Incubation of AcTat with immunoprecipitated SIRT1, 2 and 3 resulted in deacetylation of Tat lysine 50, as shown in FIG. 2A. These enzymes also deacetylate histones as determined in a standard histone deacetylase assay, as shown in FIG. 2A. All reactions contained equal amounts of AcTat as determined by immunoblotting with horseradish peroxidase-conjugated streptavidin (SA), which recognized the biotin label attached to the amino terminus of AcTat (FIG. 2A, SA-HRP). SIRT enzymes in the reactions were visualized by immunoblotting with anti-FLAG antibodies (FIG. 2A, α-FLAG).

Figure 2B:
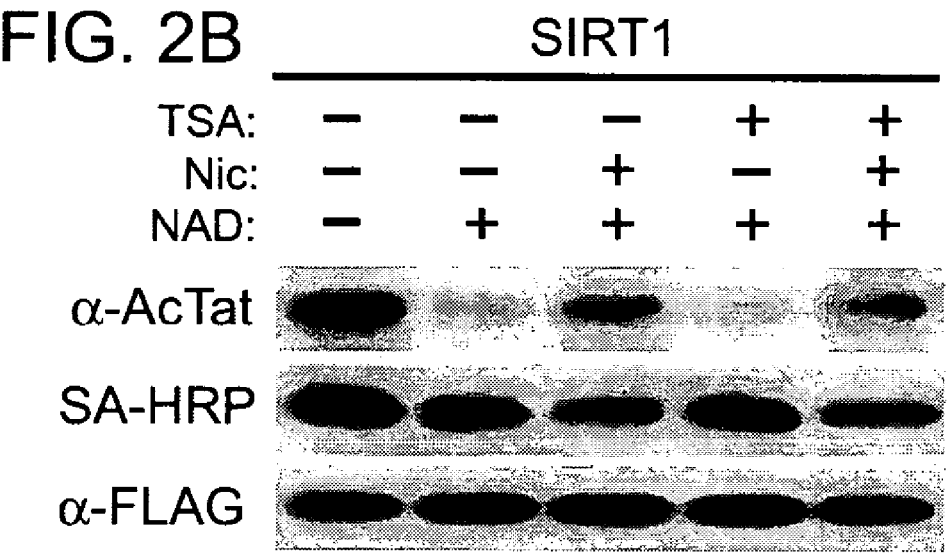

SIRT2 and 3 proteins are primarily localized in the cytoplasm and the mitochondria (North et al. (2003) Mol Cell 11: 437-444; and Schwer et al. (2002) J Cell Biol 158: 647-657); and SIRT1 resides in the cell nucleus (Langley et al. (2002) EMBO J. 21: 2383-2396; and Vaquero et al. (2004) Mol Cell 16: 93-105). Tat is a predominantly nuclear protein; thus, efforts were focused primarily on SIRT1. The SIRT1-mediated deacetylation of Tat was dependent on NAD$^+$ and completely inhibited by nicotinamide, an inhibitor for class III HDACs (Landry et al. (2000) Biochem Biophys Res Commun 278: 685-690; and Bitterman et al. (2002) J Biol Chem 277: 45099-45107). TSA, a specific inhibitor of class I and II HDACs, had no effect (FIG. 2B). These results demonstrate that the Tat deacetylase activity within immunoprecipitated SIRT1 material can be solely attributed to SIRT1 and not to a contaminating class I or II HDAC.

FIGS. 2A and 2B. In vitro Tat deacetylation by human SIRT proteins. Expression vectors for FLAG-tagged SIRT proteins were transfected into 293 cells, immunoprecipitated, and incubated with synthetic Tat (72 amino acids) carrying an N-terminal biotin label and an acetyl group at position 50 (AcTat) in the presence of nicotinamide adenine dinucleotide (NAD$^+$). Immunoprecipitated material was also analyzed in a radioactive histone deacetylase assay using an H3 peptide as a substrate. FIG. 2A. Western blot analysis of deacetylation reactions with antibodies specific for acetylated lysine 50 in Tat (α-AcTat), horseradish peroxidase-coupled streptavidin (SA-HRP) or α-FLAG antibodies. FIG. 2B. Western blotting of Tat deacetylation by immunoprecipitated SIRT1 in the presence or absence of NAD$^+$, TSA, or nicotinamide (Nic).

Figures 3A, 3B:
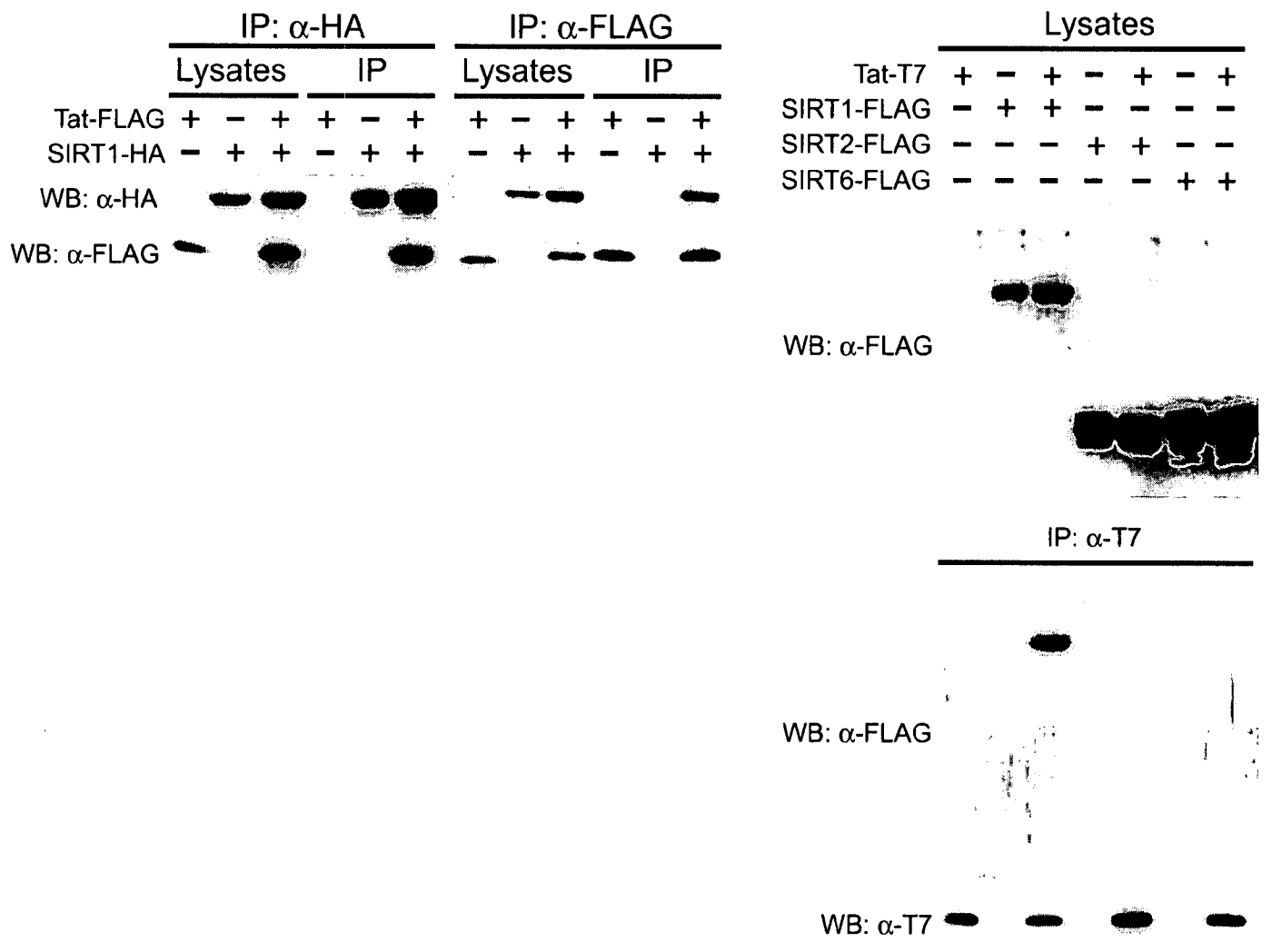
Figure 3C:
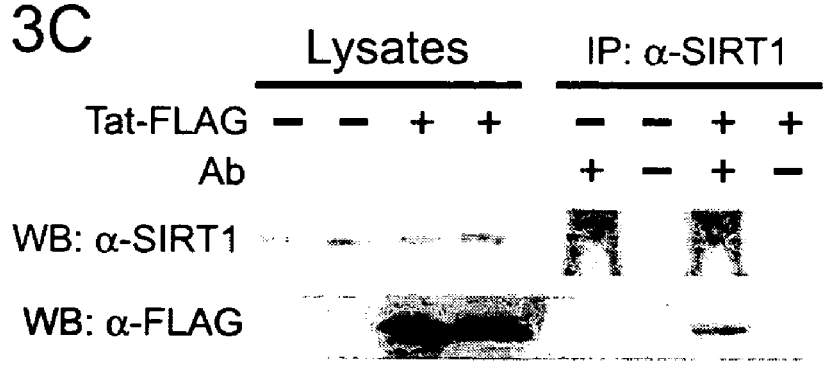

To test whether Tat and SIRT1 interact, Tat-FLAG and SIRT1-HA were overexpressed in 293 cells, and cellular lysates subjected to co-immunoprecipitation assays. Tat was detected with an α-FLAG antiserum in material immunoprecipitated with SIRT1 by the α-HA antibody in cells transfected with SIRT1- and Tat expression vectors, but no signal was obtained when SIRT1 or Tat alone was expressed (FIG. 3A, left panel). Conversely, SIRT1 also specifically co-immunoprecipitated with Tat-FLAG (FIG. 3A, right panel). The same was observed when Tat-T7 was co-expressed with SIRT1-FLAG and was immunoprecipitated with α-T7 antibodies (FIG. 3B). No co-immunoprecipitation of Tat was observed with SIRT2 and 6 (FIG. 3B), two SIRT proteins that can also localize to the cell nucleus, or any other SIRT protein. Furthermore, Tat co-immunoprecipitated with endogenous SIRT1 in Tat-expressing, but not in vector-transfected, 293 cells (FIG. 3C). No SIRT1- or Tat-specific signals were obtained after immunoprecipitations in the absence of α-SIRT1 antibodies, excluding nonspecific binding of Tat to the sepharose beads.

Figure 3D:
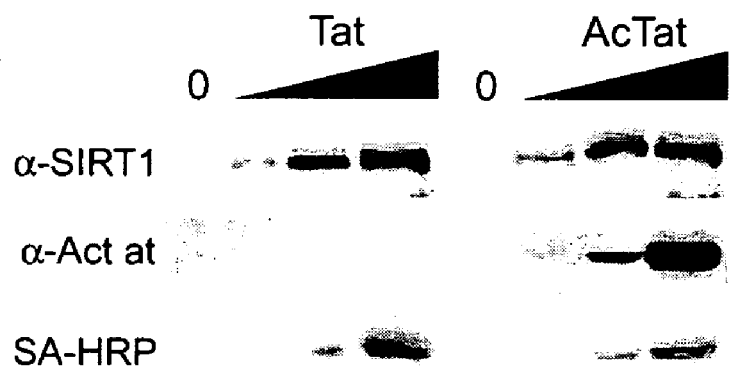
Figure 3E:
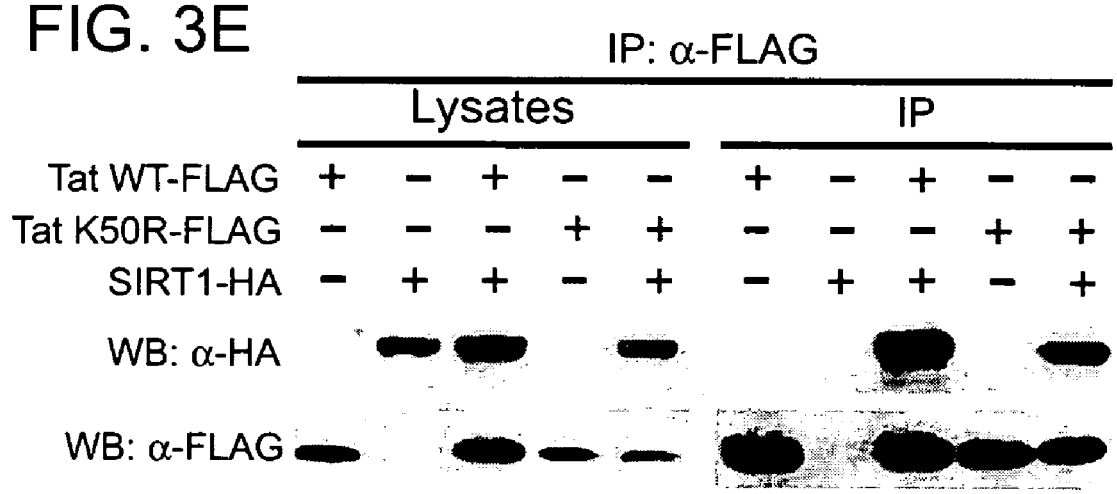

To test whether Tat and SIRT1 interacted directly, increasing amounts of biotinylated synthetic Tat (72 amino acids) were incubated with recombinant full-length SIRT1. After pulldown with streptavidin-agarose, SIRT1 co-immunoprecipitated with Tat in a dose-dependent manner (FIG. 3D). Recombinant SIRT1 bound equally well to acetylated and unacetylated synthetic Tat, indicating that the interaction occurred independently of the acetylation state of Tat (FIG. 3D). Western blotting with AcTat antibodies showed that AcTat remained acetylated during incubation with the SIRT1 enzyme (FIG. 3D). Re-blotting with streptavidin-horseradish peroxidase detected both Tat proteins in equivalent amounts in the binding reactions (FIG. 3D). The ability of a Tat mutant protein (TatK50R) to interact with SIRT1 was also tested. This mutation preserves the basic charge at position 50, but cannot be acetylated. After transfection into 293 cells, TatK50R accumulated to lower concentrations than wildtype Tat, but was bound to SIRT1 efficiently in co-immunoprecipitation assays (FIG. 3E). These results collectively indicate that Tat binds SIRT1 directly and independently of lysine 50.

FIGS. 3A-3E. Physical interaction between Tat and SIRT1. FIG. 3A. Co-immunoprecipitation/western blot analysis of FLAG-tagged Tat and HA-tagged SIRT1 after transfection of corresponding expression vectors or empty vector controls into 293 cells. FIG. 3B. The same experiments as in (FIG. 3A) performed with T7-tagged Tat and FLAG-tagged SIRT1, 2 and 6. FIG. 3C. Co-immunoprecipitation of FLAG-tagged Tat with endogenous SIRT1 in 293 cells transfected with the Tat expression vector or the empty vector control. Immunoprecipitations were performed with or without rabbit α-SIRT1 antibodies. FIG. 3D. Western blotting of recombinant SIRT1 protein after pulldown with synthetic biotinylated Tat or AcTat. Tat proteins were detected with antibodies specific for acetylated lysine 50 in the Tat ARM (α-AcTat) or horseradish peroxidase-coupled streptavidin (SA-HRP). FIG. 3E. Co-immunoprecipitation/western blotting of FLAG-tagged Tat or TatK50R with HA-tagged SIRT1.

The effects of SIRT1 on Tat function were assessed after transfection into HeLa cells. SIRT1 modestly, but reproducibly, enhanced Tat-mediated transactivation of an HIV promoter luciferase construct (FIG. 4A, left panel). In contrast, expression of a catalytically inactive SIRT1 protein (SIRT1H363Y) suppressed Tat transactivation in a dominant-negative manner, indicating that the catalytic activity of SIRT1 is necessary for Tat transactivation. Similar results were obtained when an HIV promoter reporter construct containing mutant binding sites for the transcription factor NF-κB was used (FIG. 4A, middle panel). This result indicated that the superinduction of Tat activity by wildtype SIRT1 and the suppression of Tat activity by catalytically inactive SIRT1 was dependent on the interaction between SIRT1 and Tat rather than on the interaction between SIRT1 and NF-κB/p65 (Yeung et al. (2004) EMBO J. 23: 2369-2380). Importantly, SIRT1 (wildtype and mutant) had no effect on the transcriptional activity of the Rous sarcoma virus (RSV) LTR, a promoter used to drive Tat expression in these co-transfection experiments.

Figure 4D:
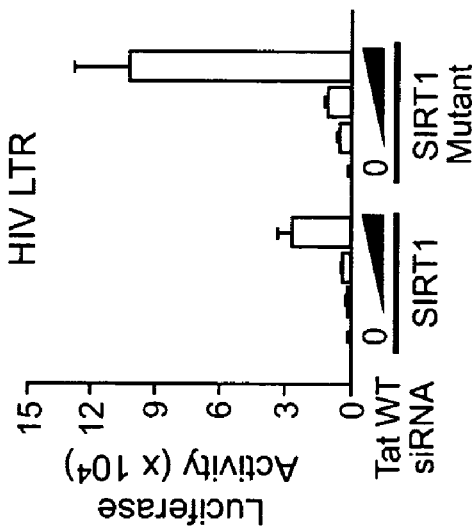
Figure 4E:
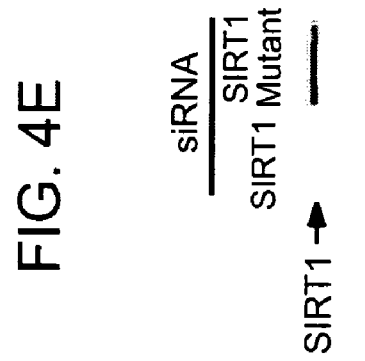

The effect of SIRT1 on Tat transactivation was further examined using siRNA-mediated knockdown of SIRT1. HeLa cells were transfected with double-stranded RNA oligonucleotides directed against SIRT1 or against GL3 luciferase as a control. All luciferase reporter constructs described in this study express GL2 luciferase, which is not affected by GL3 siRNAs (Elbashir et al. (2001) Nature 411: 494-498). Levels of endogenous SIRT1 were markedly reduced at 72 hours after transfection of siRNAs specific for SIRT1 (FIG. 4B). At this time, a significant decrease in Tat transactivation was noted in cells that had received the SIRT1 siRNA, but not the GL3 siRNA (FIG. 4C). The SIRT1 siRNA slightly enhanced the basal HIV promoter activity without Tat, and had no effect on the transcriptional activity of TatK50R, the Tat mutant that cannot be acetylated (FIG. 4C). Loss of SIRT1 had no effect on the transcriptional activity of the immediate early promoter of the cytomegalovirus (CMV) used to drive Tat expression in these experiments (FIG. 4D). In addition, Tat levels in HeLa cells transfected with SIRT1 siRNAs were comparable to Tat levels detected in cells transfected with GL3 siRNAs as determined by western blotting. To confirm the specificity of the SIRT1 siRNA, mutant double-stranded siRNA oligonucleotides were generated which contained a two-nucleotide mismatch between the target mRNA for SIRT1 and the antisense strand of the siRNA. Transfection of mutant SIRT1 siRNA did not affect expression of endogenous SIRT1 protein in HeLa cells, indicating that the mutation abrogated SIRT1 mRNA cleavage (FIG. 4E). SIRT1 siRNA, but not mutant siRNA, suppressed Tat transactivation of the HIV LTR luciferase construct, confirming that the observed suppression was dependent on the loss of SIRT1 protein (FIG. 4F).

Figure 4F:
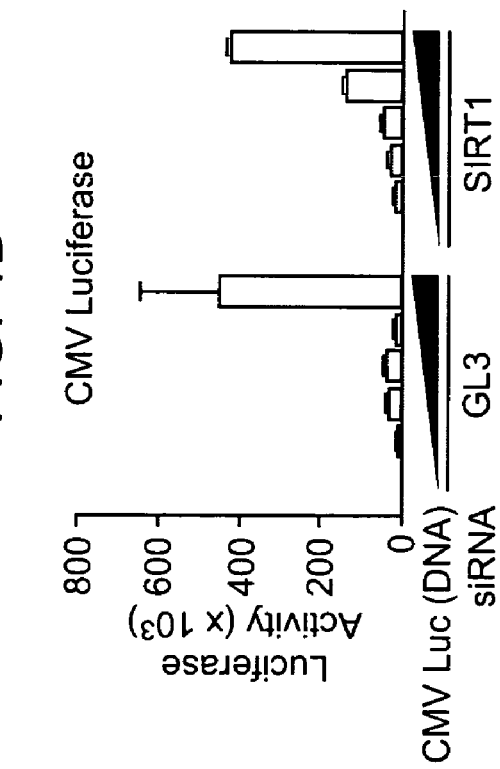

FIGS. 4A-4F. SIRT1 is a positive cofactor for Tat transactivation. FIG. 4A. Co-transfection of SIRT1 or a catalytically inactive SIRT1 mutant (SIRT1H363Y) with the HIV LTR luciferase construct and increasing amounts of a Tat expression vector (RSV-Tat, 0, 2, 20, and 200 ng), an HIV LTR luciferase construct containing mutated binding sites for the transcription factor NF-κB and RSV-Tat (20 ng) or with an RSV-luciferase construct (200 ng) in HeLa cells. The average of three experiments is shown (±SEM). FIG. 4B. Western blot analysis of HeLa cells 72 hours after transfection of siRNA oligonucleotides directed against SIRT1 or GL3. FIG. 4C. Co-transfection of the HIV LTR luciferase construct with increasing amounts of CMV-Tat or CMV-TatK50R (0, 50, 100, 200, 400, and 800 ng) 48 hours after transfection of double-stranded siRNA oligonucleotides directed against SIRT1 or GL3 luciferase in HeLa cells. Luciferase activity was measured 24 hours after plasmid transfection and 72 hours after siRNA transfection. Note that all luciferase reporter vectors used in this study express GL2 luciferase, which is not affected by GL3-specific siRNAs. The average of three experiments is shown (±SEM). FIG. 4D. The transcriptional activity of increasing amounts of the CMV-luciferase reporter (0, 50, 100, 200, 400, and 800 ng) was similar in SIRT1 knockdown or GL3-treated control cells. The average of two experiments performed in duplicate is shown (±SEM). FIG. 4E. Western blotting of endogenous SIRT1 72 hours after transfection of siRNA oligonucleotides directed against SIRT1 or mutated SIRT1 siRNA, containing a two-nucleotide mismatch. FIG. 4F. Co-transfection of the HIV LTR luciferase with increasing amounts of CMV-Tat (0, 2, 20, and 200 ng) in HeLa cells pre-transfected with wildtype or mutant SIRT1 siRNA oligonucleotides as described in FIG. 4C Since SIRT1 only modestly enhanced Tat transactivation in HeLa cells, which already express significant levels of SIRT1, the effect of SIRT1 on Tat transactivation was examined in a SIRT1-negative background. Mouse embryonic fibroblasts (MEFs) derived from SIRT1 knockout mice (McBurney et al. (2003) Mol Cell Biol 23: 38-54) were obtained. The HIV LTR luciferase reporter and the Tat expression vector were introduced into these cells by nuclear microinjections because of their low responsiveness to various transfection protocols. Because murine CyclinT1 does not support Tat transactivation (Garber et al. (1998) Genes Dev 12: 3512-3527; and Bieniasz et al. (1998) EMBO J. 17: 7056-7065), an expression vector for human CyclinT1 was included in the microinjections. A 120-fold increase in HIV promoter luciferase activity was detected in the presence of Tat and human CyclinT1 in SIRT1+/+ MEFs (FIG. 5A). In contrast, Tat-mediated transactivation of the HIV LTR was reduced in SIRT1–/– MEFs (FIG. 5A). Ectopic expression of increasing amounts of human SIRT1 resulted in a dose-dependent increase of Tat transactivation in SIRT1–/– MEFs (FIG. 5B). In contrast, transactivation of the 5×UAS promoter by Gal4-VP16 was reduced in response to SIRT1 (FIG. 5C). These results collectively demonstrate that SIRT1 represents a positive factor for Tat function.

FIGS. 5A-C. Impaired Tat transcriptional activity in murine SIRT1–/– cells. FIG. 5A. Nuclear microinjection of HIV LTR luciferase, RSV-Tat and a human CyclinT1-expressing construct or the respective empty vectors into murine embryonic fibroblasts (MEFs) derived from SIRT+/+ or SIRT–/– mice. Cells were co-injected with CMV-GFP, and the luciferase activity per GFP-positive cell was calculated. An average of two injections is shown. FIG. 5B. The HIV LTR luciferase construct together with RSV-Tat or the empty vector and the CyclinT1-expressing construct were co-injected into SIRT−/− MEFs in the presence of increasing amounts of a human SIRT1-expressing plasmid. The average of three experiments is shown (±SEM). FIG. 5C. Co-injection of the human SIRT1 expression vector or the empty vector control together with the 5×UAS luciferase construct containing five Gal4 binding sites upstream of the thymidine kinase promoter and a Gal4/VP16 expression plasmid into SIRT1−/− MEFs. The average of three experiments is shown (±SEM).

This model was further tested in nuclear microinjection experiments using synthetic full-length Tat and AcTat. Microinjection of increasing amounts of either Tat or AcTat proteins into HeLa cells caused a marked transactivation of the HIV LTR luciferase reporter in a dose-dependent manner (FIG. 6A, left panel). AcTat transactivated the HIV promoter ~1.5 to 3-fold better than Tat. Transactivation by Tat and AcTat was dependent on the bulge and loop regions of TAR, indicating that transactivation by both proteins required the formation of an intact Tat/TAR/CyclinT1 complex (Feng and Holland (1988) Nature 334: 165-167; Wei et al. (1998) Cell 92: 451-462; and Luo et al. (2000) Nature 408: 377-381) (FIG. 6A, middle and right panels). In agreement with this conclusion, transactivation by both Tat proteins was inhibited in a dose-dependent manner by 5,6-dichlorobenzimidazole riboside (DRB), a CDK9 inhibitor known to block Tat function (FIG. 6B) (Zhu et al. (1997) Genes Dev 11: 2622-2632).

AcTat cannot form the trimolecular complex with CyclinT1 and TAR RNA in vitro. It was hypothesized that AcTat becomes partially deacetylated by the Tat deacetylase upon microinjection. This would allow the initiation of the transactivation process by unacetylated Tat binding to TAR with CyclinT1 and CDK9. To further test this hypothesis, cells were treated with deacetylase inhibitors after microinjection of AcTat and the HIV promoter construct. Treatment with TSA, an inhibitor of class I and II HDACs, enhanced the transcriptional activity of AcTat as well as the basal HIV promoter activity (FIG. 6C, left panel). In contrast, nicotinamide, an inhibitor of class III deacetylases, blocked transactivation of the HIV promoter by AcTat while stimulating basal HIV promoter activity (FIG. 6C, right panel). Similarly, knockdown of SIRT1 using siRNA inhibited transcriptional activity of AcTat, while slightly enhancing Tat-mediated or basal transcriptional activity of the HIV promoter (FIG. 6D). These results support the model that the transcriptional activity of AcTat depends on deacetylation by SIRT1 in cells.

FIGS. 6A-6D. Transcriptional activity of AcTat depends on deacetylation by SIRT1. FIG. 6A. AcTat functions through TAR and CyclinT1 binding. Nuclear microinjection of increasing amounts of synthetic Tat or AcTat together with wildtype, TAR Δbulge, or TAR Δloop mutant HIV LTR luciferase constructs into HeLa cells. Cells were co-injected with CMV-GFP, and luciferase activity was calculated per GFP-positive cell. An average of three experiments is shown (±SEM). FIG. 6B. AcTat transactivation requires CDK9. HeLa cells microinjected with Tat or AcTat (each 30 ng/μl) and the HIV LTR luciferase reporter were treated with increasing amounts of 5,6-dichlorobenzimidazole riboside (DRB), a known CDK9 inhibitor, for four hours. FIG. 6C. AcTat transcriptional activity is inhibited by nicotinamide, but not TSA. HeLa cells injected with HIV LTR luciferase and increasing amounts of AcTat-were treated with TSA (400 nM) or nicotinamide (5 mM) for four hours. The average of two experiments is shown. FIG. 6D. SIRT1 is necessary for AcTat, but not Tat function. HeLa cells were transfected with siRNAs specific for SIRT1 or GL3 luciferase 48 hours before microinjection of HIV LTR luciferase and Tat or AcTat (each 30 ng/μl). The average of three experiments is shown (±SEM).

Figure 7A:
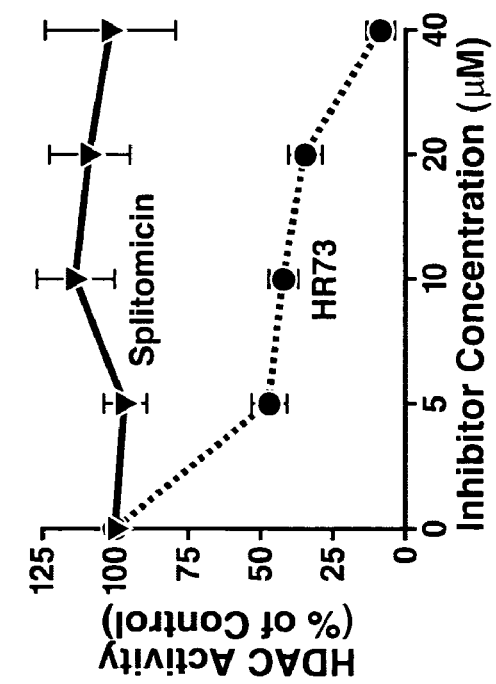
Figure 7D:
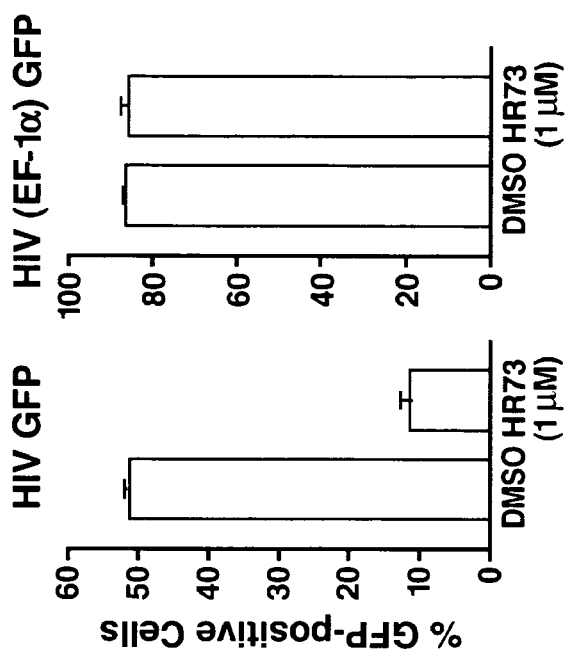
Figure 7C:
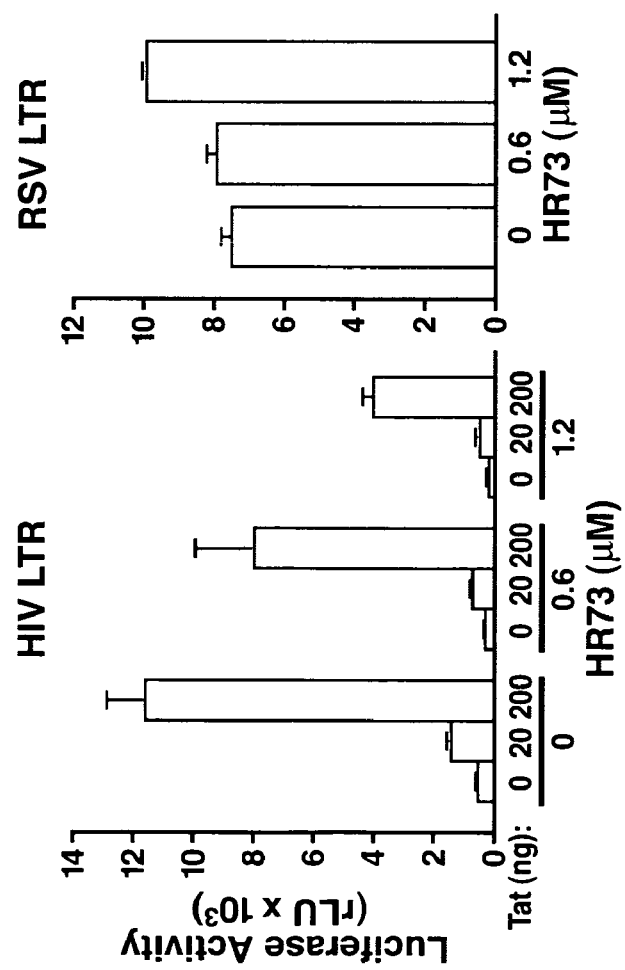

The identification of SIRT1 as an enzyme that catalyzes an important step in HIV transcription suggests that it could be targeted therapeutically. Splitomicin was identified as a small molecule inhibitor of the *S. cerevisiae* Sir2p protein. Bedalov et al. (2001) *Proc Natl Acad Sci USA* 98: 15113-15118. While splitomicin did not inhibit human SIRT1, a splitomicin derivative, called HR73, was identified which is structurally related to a previously described inhibitor of Hst1, a homologue of Sir2p in yeast. Hirao et al. (2003) *J Biol Chem* 278: 52773-52782. HR73 effectively inhibited the histone deacetylase activity of SIRT1 in vitro with an $IC_{50}$ of <5 μM (FIGS. 7A and 7B). Treatment of HeLa cells with HR73 suppressed Tat-dependent HIV transcription in a dose-dependent manner (3-fold at ~1 μM) after transfection of the Tat vector and the HIV LTR luciferase construct (FIG. 7C, left panel). In separate experiments, HR73 induced hyperacetylation of another target of SIRT1, the tumor suppressor p53, at the same concentration (1 μM). Importantly, HR73 (1 μM) did not suppress the activity of the RSV LTR, the promoter driving Tat expression in these experiments (FIG. 7C, right panel).

To examine the effect of HR73 on HIV infection, infectious HIV particles were generated, using a molecular clone of $HIV_{NL4-3}$ that contained the GFP open reading frame in place of the viral nef gene (Jordan et al. (2003) Embo J 22: 1868-1877). To restrict analysis to a single infection cycle, this clone also contained a frameshift mutation in the viral env gene. Viral particles were produced by co-transfection with a construct expressing the glycoprotein of the vesicular stomatitis virus (VSV-G). Jurkat T cells were incubated with viral supernatant for at least 18 hours, washed to remove extracellular virus, and treated with HR73 (1 μM) or DMSO alone. It was observed that HIV gene expression was reduced 5-fold in cells treated with HR73 as measured by GFP expression (FIG. 7D, left panel). In contrast, GFP expression in cells infected with an HIV-based lentiviral vector expressing GFP from the elongation factor 1α (EF-1α) promoter was not affected by HR73 treatment (FIG. 7D, right panel).

FIGS. 7A-7D. Inhibition of HIV gene expression by a small molecule inhibitor of SIRT1. FIG. 7A. In vitro histone deacetylation assays including recombinant SIRT1, radioactively labeled histone H3 peptide, and indicated concentrations of splitomicin or HR73. The average (±SEM) of two experiments performed in duplicate is shown for each point. FIG. 7B. Chemical structures of splitomicin and its derivative HR73. FIG. 7C. Inhibition of Tat transactivation by HR73. RSV-Tat (0, 20, and 200 ng) and HIV LTR luciferase (200 ng) or RSV luciferase (200 ng) vectors were transfected into HeLa cells. Transfected cells were treated with indicated concentrations of HR73 or DMSO for 8 hours. FIG. 7D. Inhibition of HIV gene expression by HR73. GFP expression in Jurkat T cells infected with $HIV_{NL4-3}$ containing the GFP open reading frame in place of the viral nef gene or with an HIV-based lentiviral vector expressing GFP from the heterologous elongation factor 1α (EF-1α) promoter. Treatment with HR73 (1 μM) or DMSO was performed for 36 hours after overnight infection. The average (±SEM) of four experiments is shown.

These data confirm the selectivity of HR73 for HIV transcription and demonstrate that other steps in the viral life cycle, including reverse transcription, nuclear import and integration remain unaffected by HR73. These experiments collectively show that the SIRT1 deacetylase activity is required for HIV gene expression and establish SIRT1 as a potential drug target in the treatment of HIV-1 infection.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An in vitro method of identifying an agent that inhibits SIRT1 Tat deacetylase activity, the method comprising:
contacting a cell that produces a SIRT1 Tat deacetylase polypeptide and an acetylated Tat polypeptide with a test agent; and
determining the level of acetylated Tat polypeptide in the cell compared to the level of acetylated Tat polypeptide in a control cell not contacted with the test agent, wherein a reduction in the level of acetylated Tat in the cell contacted with the test agent compared to the control cell indicates that the test agent inhibits SIRT1 Tat deacetylase activity.

2. The method of claim 1, wherein the Tat polypeptide is a fusion protein comprising Tat and a fusion partner selected from an immunological tag and a polyhistidine tag.

3. The method of claim 1, wherein said determining step is an immunological assay using an antibody specific for acetylated Tat.

4. A cell-free in vitro assay for identifying an agent that inhibits SIRT1 Tat deacetylase activity, the method comprising:
   contacting a test sample with a test agent, wherein the test sample comprises a SIRT1 Tat deacetylase polypeptide, an acetylated Tat polypeptide and NAD$^+$; and
   determining the level of acetylated Tat polypeptide in the test sample compared to the level of acetylated Tat polypeptide in a control sample lacking the test agent, wherein a reduction in the level of acetylated Tat polypeptide in the test sample compared to the control sample indicates that the test agent inhibits SIRT1 Tat deacetylase activity.

5. The method of claim 4, wherein said determining step is an immunological assay using an antibody specific for acetylated Tat.

6. The method of claim 1, wherein the cell is a eukaryotic cell.

7. The method of claim 6, wherein the cell is a mammalian cell.

8. The method of claim 1, wherein the cell is genetically modified to produce the SIRT1 polypeptide.

9. The method of claim 1, wherein the cell is genetically modified to produce the Tat polypeptide.

10. The method of claim 1, wherein the SIRT 1 Tat deacetylase polypeptide is a human SIRT1 Tat deacetylase polypeptide.

11. The method of claim 1, wherein the Tat polypeptide comprises the amino acid sequence Lys-(Ala or Gly)-Leu-Gly-Ile-Ser-Tyr-Gly-Arg-Lys-Lys-Arg-(Arg or Lys)-(Gln or His)-Arg-Arg-(Arg or Gly or Lys or Ser)-(Pro or Ala or Thr)-(Gln or Pro or Thr) (SEQ ID NO:1), wherein one or more of the lysines is acetylated.

12. The method of claim 1, wherein the Tat polypeptide comprises the amino acid sequence Ser-Tyr-Gly-Arg-AcLys-Lys-Lys-Arg-Arg-Gln-Arg (SEQ ID NO:2).

13. The method of claim 4, wherein the SIRT1 Tat deacetylase polypeptide is a human SIRT1 Tat deacetylase polypeptide.

14. The method of claim 4, wherein the Tat polypeptide comprises the amino acid sequence Lys-(Ala or Gly)-Leu-Gly-Ile-Ser-Tyr-Gly-Arg-Lys-Lys-Arg-(Arg or Lys)-(Gln or His)-Arg-Arg-(Arg or Gly or Lys or Ser)-(Pro or Ala or Thr)-(Gln or Pro or Thr) (SEQ ID NO:1), wherein one or more of the lysines is acetylated.

15. The method of claim 4, wherein the Tat polypeptide comprises the amino acid sequence Ser-Tyr-Gly-Arg-AcLys-Lys-Lys-Arg-Arg-Gln-Arg (SEQ ID NO:2).

16. The method of claim 4, wherein the SIRT1 polypeptide and the Tat polypeptide represent at least 80% by weight of the proteins in the sample.

* * * * *

UNITED STATES PATENT AND TRADEMARK OFFICE
CERTIFICATE OF CORRECTION

| | | |
|---|---|---|
| PATENT NO. | : 7,485,416 B2 | Page 1 of 1 |
| APPLICATION NO. | : 11/022192 | |
| DATED | : February 3, 2009 | |
| INVENTOR(S) | : Melanie Ott | |

It is certified that error appears in the above-identified patent and that said Letters Patent is hereby corrected as shown below:

Please replace the Statement Regarding Federally Sponsored Research beginning on column 1, line 17, with the following revised statement:

STATEMENT REGARDING FEDERALLY SPONSORED RESEARCH

This invention was made with government support under PO1 GM066531 awarded by the National Institutes of Health. The government has certain rights in the invention.

Signed and Sealed this

Eighth Day of June, 2010

David J. Kappos
*Director of the United States Patent and Trademark Office*

```
                          SEQUENCE LISTING

<160> NUMBER OF SEQ ID NOS: 8

<210> SEQ ID NO 1
<211> LENGTH: 19
<212> TYPE: PRT
<213> ORGANISM: Artificial Sequence
<220> FEATURE:
<223> OTHER INFORMATION: acetylated Tat polypeptide substrate
<220> FEATURE:
<221> NAME/KEY: VARIANT
<222> LOCATION: (2)...(2)
<223> OTHER INFORMATION: Xaa = Ala or Gly
<220> FEATURE:
<221> NAME/KEY: VARIANT
<222> LOCATION: (10)...(10)
<223> OTHER INFORMATION: acetylated lysine
<220> FEATURE:
<221> NAME/KEY: VARIANT
<222> LOCATION: (13)...(13)
<223> OTHER INFORMATION: Xaa = Arg or Lys
<220> FEATURE:
<221> NAME/KEY: VARIANT
<222> LOCATION: (14)...(14)
<223> OTHER INFORMATION: Xaa = Gln or His
<220> FEATURE:
<221> NAME/KEY: VARIANT
<222> LOCATION: (17)...(17)
<223> OTHER INFORMATION: Xaa = Arg or Gly or Lys or Ser
<220> FEATURE:
<221> NAME/KEY: VARIANT
<222> LOCATION: (18)...(18)
<223> OTHER INFORMATION: Xaa = Pro or Ala or Thr
<220> FEATURE:
<221> NAME/KEY: VARIANT
<222> LOCATION: (19)...(19)
<223> OTHER INFORMATION: Xaa = Gln or Pro or Thr

<400> SEQUENCE: 1

Lys Xaa Leu Gly Ile Ser Tyr Gly Arg Lys Lys Arg Xaa Xaa Arg Arg
 1               5                  10                  15

Xaa Xaa Xaa

<210> SEQ ID NO 2
<211> LENGTH: 11
<212> TYPE: PRT
<213> ORGANISM: Artificial Sequence
<220> FEATURE:
<223> OTHER INFORMATION: acetylated Tat polypeptide substrate
<220> FEATURE:
<221> NAME/KEY: ACETYLATION
<222> LOCATION: (5)...(5)
<223> OTHER INFORMATION: acetylated Lysine

<400> SEQUENCE: 2

Ser Tyr Gly Arg Lys Lys Lys Arg Arg Gln Arg
 1               5                  10

<210> SEQ ID NO 3
<211> LENGTH: 28
<212> TYPE: DNA
<213> ORGANISM: Artificial Sequence
```

```
-continued

<220> FEATURE:
<223> OTHER INFORMATION: primer

<400> SEQUENCE: 3
cctatggcag gaggaagcgg agacagcg                                          28

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
cgctgtctcc gcttcctcct gccatagg                                          28

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
ggttagacca gaactgagcc tgggagc                                           27

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
gctcccaggc tcagttctgg tctaacc                                           27

<210> SEQ ID NO 7
<211> LENGTH: 44
<212> TYPE: DNA
<213> ORGANISM: Artificial Sequence
<220> FEATURE:
<223> OTHER INFORMATION: primer

<400> SEQUENCE: 7
ggttagacca gatctgagca gggtagctct ctggctaact aggg                        44

<210> SEQ ID NO 8
<211> LENGTH: 44
<212> TYPE: DNA
<213> ORGANISM: Artificial Sequence
<220> FEATURE:
<223> OTHER INFORMATION: primer

<400> SEQUENCE: 8
ccctagttag ccagagagct accctgctca gatctggtct aacc                        44
```